(12) United States Patent
Caponetti et al.

(10) Patent No.: US 9,138,407 B2
(45) Date of Patent: Sep. 22, 2015

(54) INHALATORY PHARMACEUTICAL COMPOSITIONS IN FORM OF DRY POWDERS, SOLUTIONS OR SUSPENSIONS OBTAINED FROM THE SAME AND PROCESS FOR THEIR PREPARATION

(75) Inventors: Giovanni Caponetti, Piacenza (IT); Loretta Maggi, Placenza (IT); Laura Zanellotti, Placenza (IT); Cristina Veneziani, Sarmato (IT)

(73) Assignee: Eratech S.R.L., Milan (IT)

( * ) Notice: Subject to any disclaimer, the term of this patent is extended or adjusted under 35 U.S.C. 154(b) by 886 days.

(21) Appl. No.: 12/090,899

(22) PCT Filed: Oct. 20, 2006

(86) PCT No.: PCT/EP2006/067619
§ 371 (c)(1),
(2), (4) Date: Apr. 21, 2008

(87) PCT Pub. No.: WO2007/045689
PCT Pub. Date: Apr. 26, 2007

(65) Prior Publication Data
US 2008/0226736 A1    Sep. 18, 2008

(30) Foreign Application Priority Data

Oct. 21, 2005 (IT) .............................. MI2005A1999

(51) Int. Cl.
*A61K 9/14* (2006.01)
*A61K 9/00* (2006.01)
*A61K 45/06* (2006.01)

(52) U.S. Cl.
CPC ............. *A61K 9/0078* (2013.01); *A61K 9/0075* (2013.01); *A61K 45/06* (2013.01)

(58) Field of Classification Search
CPC .... A61K 45/06; A61K 9/0075; A61K 9/0078
See application file for complete search history.

(56) References Cited

U.S. PATENT DOCUMENTS

| | | | |
|---|---|---|---|
| 6,309,623 B1 * | 10/2001 | Weers et al. | 424/45 |
| 2002/0103139 A1 | 8/2002 | Weisspapir et al. | |
| 2007/0065373 A1 * | 3/2007 | Morton et al. | 424/46 |
| 2007/0224276 A1 * | 9/2007 | Caponetti et al. | 424/489 |
| 2011/0123574 A1 * | 5/2011 | Basu et al. | 424/400 |

FOREIGN PATENT DOCUMENTS

| | | |
|---|---|---|
| JP | H07-299141 A | 11/1995 |
| JP | H10-513174 A | 12/1998 |
| JP | 2001-517691 A | 10/2001 |
| JP | 2002-518432 A | 6/2002 |
| JP | 2003-507410 A | 2/2003 |
| JP | 2003-513031 A | 4/2003 |
| JP | 2003-516822 A | 5/2003 |
| JP | 2004-501183 A | 1/2004 |
| JP | 2005-520843 A | 7/2005 |
| WO | WO-96/23485 A1 | 8/1996 |
| WO | WO-99/16419 A1 | 4/1999 |
| WO | 99/66903 A | 12/1999 |
| WO | WO-01/13891 A2 | 3/2001 |
| WO | WO-01/32144 A1 | 5/2001 |
| WO | WO-01/43800 A1 | 6/2001 |
| WO | 01/85137 A | 11/2001 |
| WO | WO-02/00197 A1 | 1/2002 |
| WO | WO-03/079885 A2 | 10/2003 |
| WO | 2004/030659 A | 4/2004 |
| WO | 2004/060351 * | 7/2004 |
| WO | WO-2004/060351 A2 | 7/2004 |
| WO | WO-2004/093848 A2 | 11/2004 |
| WO | WO-2005/025550 A1 | 3/2005 |
| WO | 2005/102283 A | 11/2005 |

OTHER PUBLICATIONS

2011 The United States Pharmacopeia Convention (copy attached) [USPC].*
Gabrielle Pilcer et al., "Formulation and Characterization of Lipid-Coated Tobramycin Particles for Dry Powder Inhalation," Pharmaceutical Research, Kluwer Academic Publishers-Plenum Publishers, NE, vol. 23, No. 5, May 2, 2006.
Najafabadi et al., "The effect of vehicle on physical properties and aerosolisation behaviour of disodium cromoglycate microparticles spray dried alone or with L-leucine", International Journal of Pharmaceutics, 285 (2004) 97-108.

* cited by examiner

*Primary Examiner* — Suzanne Ziska
(74) *Attorney, Agent, or Firm* — Novak Druce Connolly Bove + Quigg LLP

(57) ABSTRACT

Provided is an inhalatory pharmaceutical composition that comprises a drug, a soluble excipient and a surfactant, wherein the soluble excipient is present in an amount between 10% and less than 100% by weight; and the solid excipient forms a solid matrix in which the drug is dispersed; the weight ratio between the surfactant and drug is between 0.01 and 10; the particle size of at least 50% of the particles of the powder is below 5 μm; the bulk density $d_b$ of the powder is between 0.1 and 0.3 g/cc; the tapped density $d_t$ of the powder is between 0.15 and 0.7 g/cc and the ratio $d_b/d_t$ is between 0.2 and 0.65. Also provided is the method for fabricating the composition.

40 Claims, 6 Drawing Sheets

Example 14: Budesonide 1.0%; Maltodextrin 97.0%; Tween 80 2.0%

(A)

(B)

Example 18: Formoterol fumarate 0.08%; Tween 80 0.5%; L-Leucine 30%; Lactose 69.42%

(A)

(B)

Example 21: Ceftazidime 50%; Tween 80 0.5%; L-Leucine 15%; Lactose 34.5%

Example 22: Colistine 40%; Tween 80 0.4%; L-Leucine 15%; Lactose 44.6%

Example 24: Ceftazidime 20%; Tween 80 0.5%; L-Leucine 15%; Lactose 64.5%

Example 25: Ceftazidime 79.2%; L-Leucine 20.0%; Tween 80 0.8%

Example 26: Ceftazidime 84.1%; L-Leucine 15.0%; Tween 80 0.9%

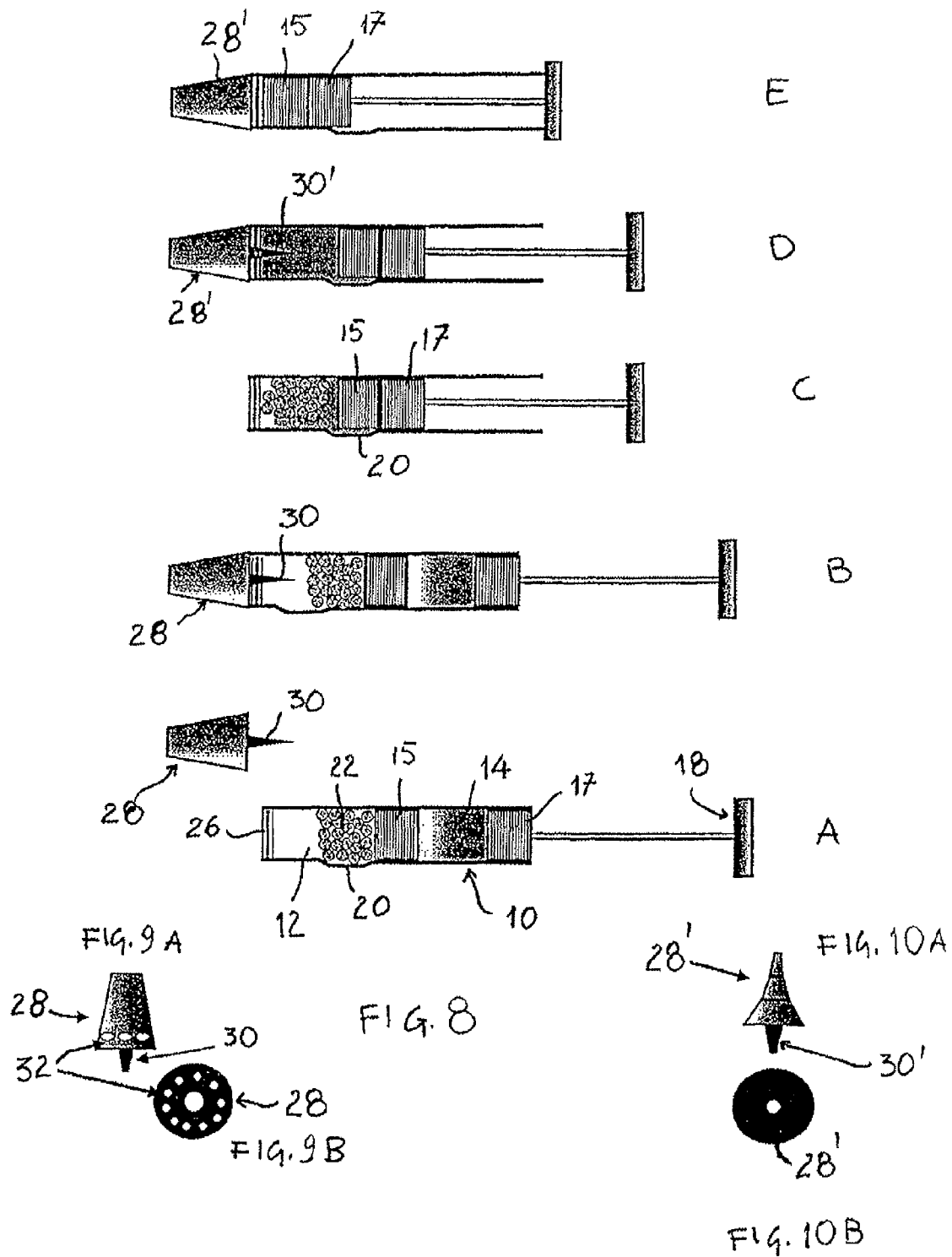

INHALATORY PHARMACEUTICAL COMPOSITIONS IN FORM OF DRY POWDERS, SOLUTIONS OR SUSPENSIONS OBTAINED FROM THE SAME AND PROCESS FOR THEIR PREPARATION

CROSS REFERENCE TO RELATED APPLICATIONS

This application is a National Phase filing under 35 U.S.C. §371 of PCT/EP2006/067619 filed Oct. 20, 2006, which claims priority to Patent Application No. MI2005A001999, filed in Italy on Oct. 21, 2005. The entire contents of each of the above-applications are incorporated herein by reference.

The present invention relates to inhalatory pharmaceutical compositions in form of dry powder, to be administered by inhalation as such or after dispersion in a liquid medium by means of a nebulizer and characterized by high delivery, respirability and stability.

Inhalation therapy with aerosols is used to deliver active ingredients in the respiratory tract, in the mucosal, tracheal and bronchial regions. The term "aerosol" describes a nebulized liquid preparation consisting of fine particles carried by a gas, usually air, to the site of therapeutic action. When the sites of the therapeutic action are the pulmonary alveoli and small bronchi, the drug must be dispersed as droplets or particles with size smaller than 5 μm as mean diameter. When the target is the pharyngeal region, coarser particles are more suitable. Suitable conditions for such treatments are represented by bronchospasm, low compliance, mucosal edema, pulmonary infections, and similar. Nowadays the administration of drugs in the lower pulmonary region is achieved through inhalation devices such as:

Nebulizers, in which the drug is dissolved or dispersed in suspension form and delivered in the lung as fine nebulized particles;

Dry powder inhalers, capable of delivering the drug loaded in the device as dry micronized particles; or Pressurized inhalers, for which the drug—again in the form of small solution or suspension droplets—is delivered to the lower pulmonary region by an inert gas rapidly expanded in the air from a pressurized device.

In all this cases, technological problems were found in the development of efficient and effective products, problems which still limit inhalatory delivery of drugs.

From a clinical point of view an ideal inhalation product should be able to be taken by the patient following different administration modes, since the inhalers described are generally suitable for different kinds of patients and administration conditions. In general nebulizers are mostly used by elderly or pediatric patients, while dry powders or pressurized inhalers are more suitable for adults. The use of nebulizers is however still considered effective, since the patient inhales the drug under rest conditions and without forcing the inhalatory act, which is instead necessary when taking a powder for inhalation. Instead, in case of a pressurized inhaler, the inspiration must be coordinated with the activation of the device, to assure that the delivered particles do not impact on the bottom of the throat instead of reaching the deep lung.

For these reasons, usually, inhalatory formulations loaded in these three types of devices are substantially different from each other.

Formulations for nebulizers are basically solutions or suspensions containing excipients as salts, surfactants and preservatives that assure isotonicity of the product, homogeneity of the particle size distribution in case of a suspension, and preservation from microbial contamination.

Formulations for pressurized inhalers usually contain surfactants, propellants and co-solvents. In formulations for dry powder inhalers the excipients essentially consist of lactose with different particle size, used as a diluent.

Such formulative limitations have therefore limited the industrial development of inhalation products and, besides steroids which exist in basically all the inhalatory forms, for bronchodilator and anticholinergic active ingredients some forms are not commercialized. This formulative limit turns out to be particularly important since the current respiratory therapy makes use of combination of different kinds of drugs as a most efficient technique. So far, however, it has possible to create just two corticosteroid-bronchodilator combinations, and only in an inhalatory powder form.

With respect to nebulized formulations, the combination is left to the extemporaneous association by the patient of different formulated products, sometimes incompatible among each other.

From a therapeutic point of view it is therefore limiting for a patient not being able to take the same drug in different life conditions, such as at home, at work, while travelling and in case of emergency. For said different situations, it could happen that the patient has to use different products containing different active ingredients.

Among the various problems encountered in the development of inhalatory products, the most important relates to the chemical stability against atmospheric agents, which causes a rapid degradation of the inhalatory formulation and consequentially a short shelf life of the contained product.

The stability of an inhalation product is particularly important since it must be delivered to the deep lung while retaining its physical features in order to achieve a quantitative deposition of particles or droplets in its deepest regions.

It must be added that the number of excipients currently approved for inhalation administration and therefore non-toxic for the pulmonary tissue is extremely limited.

In the literature examples are reported of dry inhalation powders endowed of high dispersibility in air due to their low density.

Such powders are usually formulated with a high content of phospholipids, in particular dipalmitoylphosphatidylcholine (DPPC).

A powder of this kind is described in the patent application US2005/0074498 A1, relative to low density particles, with an internally hollow morphology, obtained by spray-drying using surfactants such as phospholipids in combination with a blowing agent. The hollow structure is described as the result of the exact combination of the blowing agent and of the surfactant phospholipid. There are no examples of similar morphology obtained without phospholipids. The use of phospholipids as surfactants imparts the main features to the product obtained and above all its sensitivity and stability against atmospheric agents, that in this case will be particularly influenced by humidity. Patent literature (US 2001/0036481 A1) indicates moreover values of the phospholipid glass transition temperature in presence of humidity of 41° C. for DPPC, 55° C. for distearoylphosphatidylcholine (DSPC) and 63° C. for dipalmitoylphosphatidylethanolamine (DPPE), the three most compatible phospholipids for pulmonary administration. These Tg values are all much lower than the characteristic Tg value of amorphous lactose. Therefore, the solution of making porous particles with phospholipids to be administered by inhalation does not seem to be supported by reasonable scientific evaluations related to long time stability of the product.

The mentioned patent application, besides its application as dry powder for inhalation, describes also an application of the same particles in an inhaler in combination with a propellant gas. The same administration would be impossible to achieve with a conventional nebulizer dispersing the particles in water or aqueous solution due to the incompatibility of the materials and above all because of the tendency to float on the liquid surface.

The concept of "high porosity" or "low density" has been used practically equivalently in the mentioned patent applications.

In particular, the term "density" has not been used with reference to the absolute density of the particles, since this, measured with a helium pycnometer, would identify the density of the solid materials that are part of the powder and the particles following the equation $$\rho=P/V(g/cc)$$

Instead, the term "density" has been used with reference to the "envelope density" of the particle, considering its hindrance volume, namely the ratio of the mass of a particle to the "envelope volume" of the particle. Considering the technical difficulty to measure the envelope density for every single particle, especially in the case of non spherical ones, the mentioned patent applications have referred to volume (and subsequently to density) parameters of the powder such as bulk volume and tapped volume.

WO 03/0350030 A1 describes the preparation of a kit for inhalatory administration which takes into consideration the preparation of a solid dry form including a drug prepared by freeze-drying a solution. The process, described also through examples, shows important industrial difficulties and above all, does not guarantee that a substantial improvement of the drug stability over time would be achieved. Upon freeze-drying, the drug included in the formulation is dispersed in a network of excipient characterized by a high porosity not modulable or changeable through the process. Said porosity, though useful for a rapid dissolution of the solid form, exposes the drug much more to atmospheric agents, compromising its stability. In the specific case there are no data on the porosity of the obtained freeze-dried products of the examples, but literature data obtained with indirect measurements set the apparent density (related to the bulk density) of freeze-dried tablets containing sugars and surfactants between 0.05 and 0.2 g/cc.

In the light of all the considerations above, it would be advantageous to produce in a single industrial process an inhalatory formulation that can be used with different inhalation ways. Such advantage would be remarkable if one of the administration ways included taking the product either as a powder as such or dispersed/dissolved in a liquid through a nebulizer, possibly with other active ingredients.

There remains, however, the unsolved or unsatisfactorily solved problem of developing an inhalatory formulation of drugs which is stable and administrable either as a dry powder or in a solution or suspension form through a nebulizer, with high delivery and respirability, and that is produced with a commercially viable process.

A first aspect of the present invention is therefore that of providing a inhalatory pharmaceutical composition including a drug, a soluble excipient and a surfactant, characterized by:
- said soluble excipient is present in an amount between 10% and less than 100% by weight;
- the weight ratio between said surfactant and said drug is between 0.01 and 10;
- the particle size of at least 50% of the particles of said powder is below 5 µm;
- the bulk density $d_b$ of said powder is between 0.1 and 0.3 g/cc;
- the tapped density $d_t$ of said powder is between 0.15 and 0.7 g/cc
- the ratio $d_b/d_t$ is between 0.2 and 0.65.

Another aspect of the invention relates to a preparation process of said pharmaceutical powder composition by spray-drying a solution of said drug with the soluble excipient.

A further aspect of the invention is an extemporaneous solution or suspension for inhalation, prepared bringing into contact said pharmaceutical powder composition with a suitable volume of liquid.

A further aspect of the invention is a kit for an extemporaneous preparation of a solution or a suspension for inhalatory use, including an suitable amount of said pharmaceutical composition and a suitable volume of liquid, and that could be also used for the direct administration of the powder without further manipulation.

BRIEF DESCRIPTION OF THE DRAWINGS

FIGS. 8A-E illustrate a delivery device according to the invention where different operative positions marked.

FIG. 9A shows the mouthpiece (28) in elevation position.

FIG. 9B shows the mouthpiece (28) in section from the top.

FIGS. 10A and 10B show the mouthpiece (28) respectively from elevated position and in section from the top.

Figure 1:
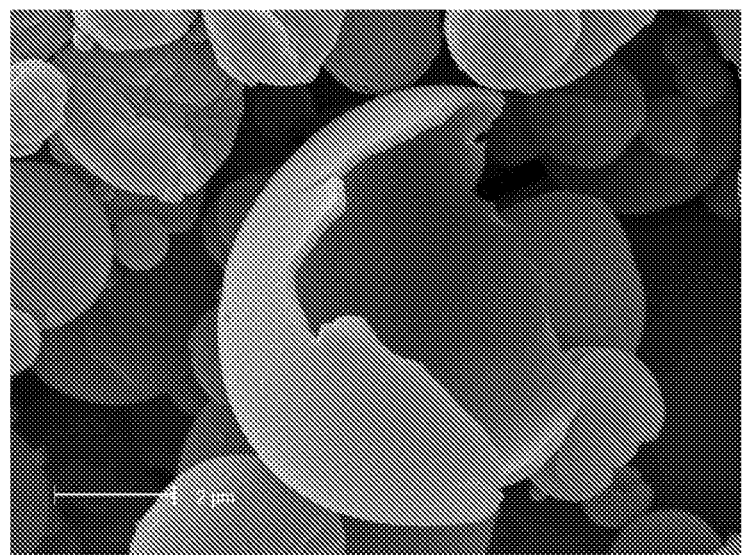
FIGS. 1A & B are electron microscope photographs of the particles from example 14 at different enlargements.
Figure 1:
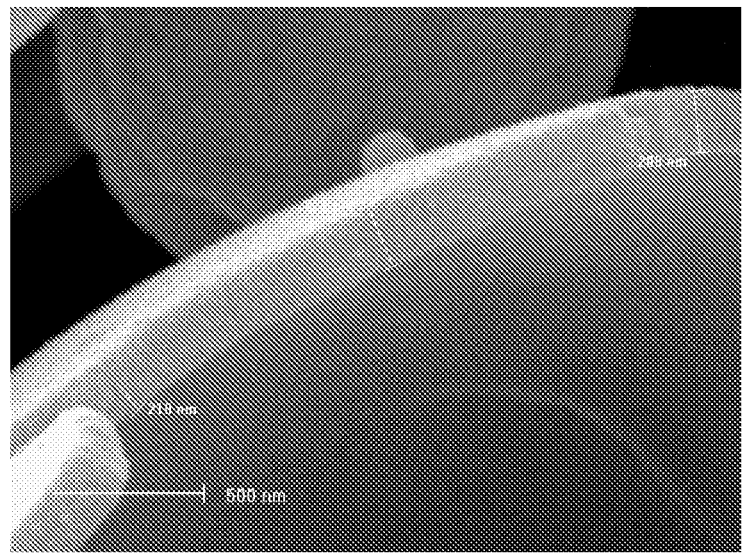
Figure 2:
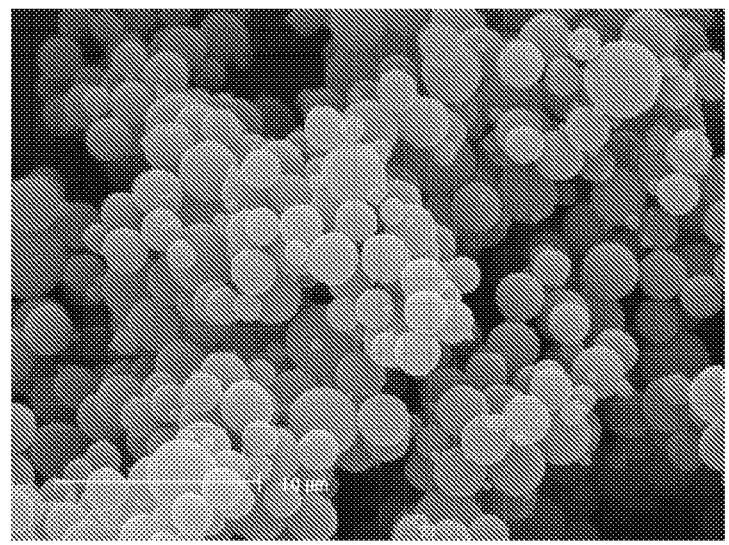
FIGS. 2A & B are electron microscope photographs of the particles from example 18 at different enlargements.
Figure 2:
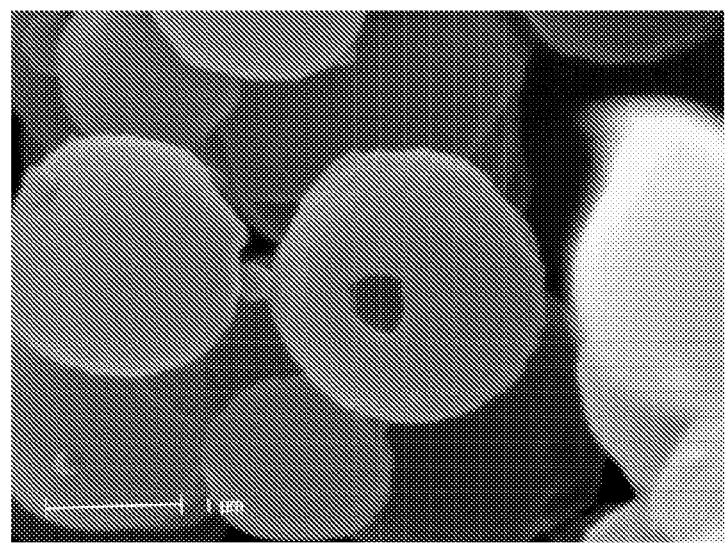
Figure 3:
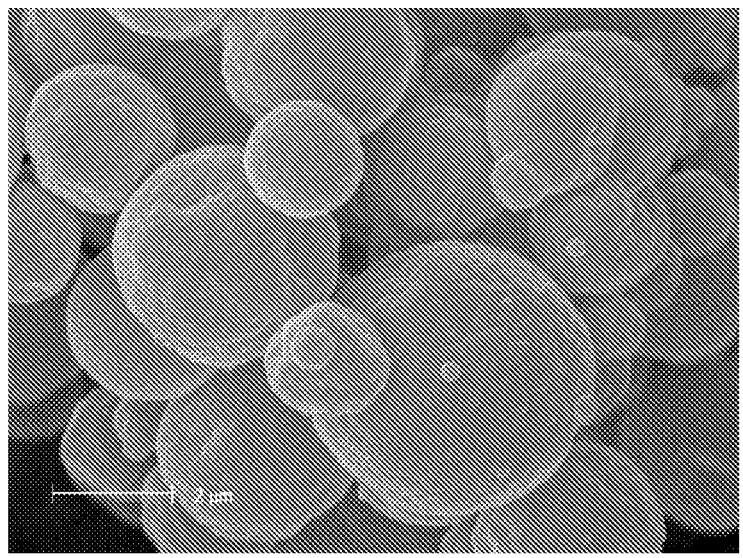
FIG. 3 is an electron microscope photograph of the particles from example 21.
Figure 4:
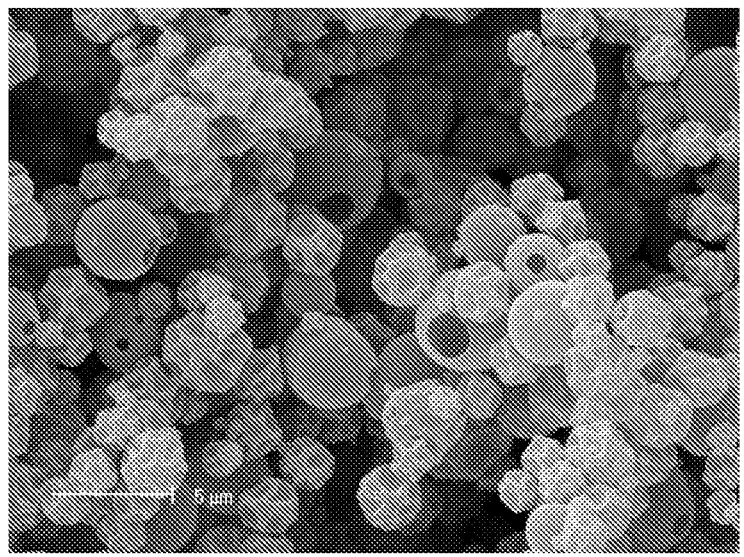
FIG. 4 is an electron microscope photograph of the particles from example 22.

With respect to the therapeutic aspect, some advantages can be found in the use of the same product both as dry powder and nebulized, since the patient makes use of the same product for any need without having to use other products. Other therapeutic advantages are related to the possibility to combine drugs of different kinds to be administered as a liquid, and to achieve a tailor-made therapy for each patient. In case of administration as a dry powder, the preparation must have proper aerodynamic features to allow for a quick aerosolization of the product with a minimum inhalatory effort from the patient.

In case of administration as a liquid, the same preparation must allow for a quick dispersion of the powder to obtain a micro suspension or a solution of the drug in a very short time and without any effort for the patient. The dry formulation must already contain all those excipients capable to assure an efficient and quantitative atomization of the product, compatible with every kind of nebulizer. The patent literature that deals with inhalation powders does not exclude in some cases the possibility that certain particles be dispersed in an aqueous medium for nebulization, but this solution actually indicates that the liquid contains beforehand possible excipients that assure an efficient nebulization of the product. In an ideal case, instead, the dispersion phase does not include substantial modifications of the liquid to allow its nebulization with different kinds of nebulizers. The formulation contains as excipients, since the very beginning, materials that help the atomization with every kind of nebulizer, thereby optimizing the quantity of drug delivered over time and the aerodynamic features of the nebulized product, besides the dispersion of the particles and the stability.

Regarding stability, in fact, the drug is trapped into a matrix of excipients which assure at the same time the stability of the dry-state product during its manipulation and its shelf life, avoiding to stock the product in temperature and humidity-controlled conditions.

Another aspect of the invention is a dose kit for the administration of a drug in a powder form, in case of need of the patient, or optionally as a dispersion in water for an easy transfer in a nebulizer ampoule. Preferably, the kit includes a delivery device in which the required components, in dosed quantities, are kept separated and are brought in contact just before their use.

The preferred manufacturing process of the dry-state powder according to the invention is by spray-drying, starting from an aqueous solution of lactose and a surfactant in which the drug is dissolved or dispersed, as to form a suspension or an emulsion.

The preferred morphology is that of an internally hollow particle to obtain a reduced bulk density.

Such solution allows indeed to improve two fundamental aspects of inhalatory administration. In case of administration in a powder form, the reduced density allows for a quick aerosolization of the powder, because of the reduced aerodynamic diameter of such particles.

In case of administration after dissolution of the powder, the hollow morphology assures a quick dissolution of the powder matrix and consequent release of the active ingredient in solution or micronized suspension.

The preferred particle size for such powder provides therefore that at least 50% of the size distribution ($X_{50}$) is placed below 5 μm, also to increase the surface area exposed to the liquid and, in case of administration in powder-form, to optimize the deposition in the deep lung.

The stable solution/suspension of the active ingredient obtainable after an extemporaneous dispersion of a solid dry pharmaceutical composition according to the invention in an aqueous medium, is such that the delivery with a pneumatic nebulizer of a standard dose of said solution or suspension in a Multi Stage Liquid Impinger at 30 lpm for 5 minutes, involves a deposited fraction in said Multi Stage Liquid Impinger calculated as Active Fraction (A.F.) of at least 25%, as it will be described further ahead.

According to the invention, the term “drug” or “active ingredient” refers to any substance that has a desired therapeutical or biological effect.

Examples of pharmacologically active ingredients that can be administered through inhalation include: $\beta_2$ agonists (e.g. salbutamol, terbutaline, clenbuterol, salmeterol, formoterol); steroids such glycocorticosteroids, preferably anti-inflammatory drugs (e.g. Ciclesonide, Mometasone, Flunisolide, Triamcinolone, Beclomethasone, Budesonide, Fluticasone); anticholinergic drugs (e.g. ipratropium, tiotropium, oxitropium); leukotriene antagonists (e.g. zafirlukast, montelukast, pranlukast); xantines (e.g. aminophylline, theobromine, theophylline); Mast cell stabilizers (e.g. cromoglicate, nedocromil); inhibitors of leukotriene synthesis (e.g. azelastina, oxatomide ketotifen); mucolytics (e.g. N-acetylcysteine, carbocysteine); antibiotics, (e.g. Aminoglycosides such as, amikacin, gentamicin, kanamycin, neomycin, netilmicin streptomycin, tobramycin; Carbacephem such as loracarbef, Carbapenems such as ertapenem, imipenem/cilastatin meropenem; Cephalosporins-first generation—such as cefadroxil, cefaxolin, cephalexin; Cephalosporins-second generation—such as cefaclor, cefamandole, defoxitin, cefproxil, cefuroxime; Cephalosporins-third generation-cefixime, cefdinir, ceftaxidime, defotaxime, cefpodoxime, ceftriaxone; Cephalosporins—fourth generation—such as maxipime; Glycopeptides such as vancomycin, teicoplanin; Macrolides such as azithromycin, clarithromycin, Dirithromycin, Erythromycin, troleandomycin; Monobactam such as aztreonam; Penicillins such as Amoxicillin, Ampicillin, Azlocillin, Carbenicillin, Cloxacillin, Dicloxacillin, Flucloxacillin, Mezlocillin, Nafcillin, Penicillin, Piperacillin, Ticarcillin; Polypeptides such as bacitracin, colistin, polymyxin B; Quinolones such as Ciprofloxacin, Enoxacin, Gatifloxacin, Levofloxacin, Lomefloxacin, Moxifloxacin, Norfloxacin, Ofloxacin, Trovafloxacin; Sulfonamides such as Mafenide, Prontosil, Sulfacetamide, Sulfamethizole, Sulfanilimide, Sulfasalazine, Sulfisoxazole, Trimethoprim, Trimethoprim-Sulfamethoxazole Co-trimoxazole (TMP-SMX); Tetracyclines such as Demeclocycline, Doxycycline, Minocycline, Oxytetracycline, Tetracycline; Others such as Chloramphenicol, Clindamycin, Ethambutol, Fosfomycin, Furazolidone, Isoniazid, Linezolid, Metronidazole, Nitrofurantoin, Pyrazinamide, Quinupristin/Dalfopristin, Rifampin, Spectinomycin); pain relievers in general such as analgesic and antiinflammatory drugs, including steroids (e.g. hydrocortisone, cortisone acetate, prednisone, prednisolone, methylpredniso lone, dexamethasone, betamethasone, triamcino lone, beclometasone, fludrocortisone acetate, deoxycorticosterone acetate, aldosterone); and non-steroid antiinflammatory drugs (e.g. Salicylates such as aspirin, amoxiprin, benorilate, coline magnesium salicylate, diflunisal, faislamine, methyl salicylate, salicyl salicylate); Arylalkanoic acids such as diclofenac, aceclofenac, acematicin, etodolac, indometacin, ketorolac, nabumetone, sulindac tolmetin; 2-Arylpropionic acids (profens) such as ibuprofen, carprofen, fenbufen, fenoprofen, flurbiprofen, ketoprofen, loxoprofen, naproxen, tiaprofenic acid; N-arylanthranilic acids (fenamic acids) such as mefenamic acid, meclofenamic acid, tolfenamic acid; Pyrazolidine derivatives such as phenylbutazone, azapropazone, metamizole, oxyphenbutazone; Oxicams such as piroxicam, meloxicam, tenoxicam; Coxib such as celecoxib, etoricoxib lumiracoxib parecoxib rofecoxib (withdrawn from market), valdecoxib (withdrawn from market); Sulphonanilides such as nimesulide; others such as licofelone, omega-3 fatty acids; cardiovascular drugs such as glycosides (e.g. strophantin, digoxin, digitoxin, proscillaridine A); respiratory drugs; antiasthma agents; bronchodilators (adrenergics: albuterol, bitolterol, epinephrine, fenoterol, formoterol, isoetharine, isoproterenol, metaproterenol, pirbuterol, procaterol, salmeterol, terbutaline); anticancer agents (e.g. cyclophosphamide, doxorubicine, vincristine, methotrexate); alkaloids (i.e. ergot alkaloids) or triptans such as sumatriptan, rizatriptan, naratriptan, zolmitriptan, eletriptan and almotriptan, than can be used against migraine; drugs (i.e. sulfonylurea) used against diabetes and related dysfunctions (e.g. metformin, chlorpropamide, glibenclamide, glicliazide, glimepiride, tolazamide, acarbose, pioglitazone, nateglinide, sitagliptin); sedative and hypnotic drugs (e.g. Barbiturates such as secobarbital, pentobarbital, amobarbital; uncategorized sedatives such as eszopiclone, ramelteon, methaqualone, ethchlorvynol, chloral hydrate, meprobamate, glutethimide, methyprylon); psychic energizers; appetite inhibitors (e.g. amphetamine); antiarthritis drugs (NSAIDs); antimalaria drugs (e.g. quinine, quinidine, mefloquine, halofantrine, primaquine, cloroquine, amodiaquine); antiepileptic drugs and anticonvulsant drugs such as Barbiturates, (e.g. Barbexaclone, Metharbital, Methylphenobarbital, Phenobarbital, Primidone), Succinimides (e.g. Ethosuximide, Mesuximide, Phensuximide), Benzodiazepines, Carboxamides (e.g. Carbamazepine, Oxcarbazepine, Rufinamide) Fatty acid derivatives (e.g. Valpromide, Valnoctamide); Carboxilyc acids (e.g. Valproic acid, Tiagabine); Gaba analogs (e.g. Gabapentin, Pregabalin, Progabide, Vigabatrin); Topiramate, Ureas (e.g. Phenacemide, Pheneturide), Carbamates (e.g. emylcamate Felbamate, Meprobamate); Pyrrolidines (e.g. Levetiracetam Nefiracetam, Seletracetam); Sulfa drugs (e.g. Acetazolamide, Ethoxzolamide, Sultiame, Zonisamide) Beclamide; Paraldehyde, Potassium bromide; antithrombotic drugs such as Vitamin K antagonist (e.g. Acenocoumarol, Dicumarol, Phenprocoumon, Phenindione, Warfarin); Platelet aggregation inhibitors (e.g. antithrombin III, Bemiparin, Deltaparin, Danaparoid, Enoxaparin, Heparin, Nadroparin, Pamaparin, Reviparin, Tinzaparin); Other platelet aggregation inhibitors (e.g. Abciximab, Acetylsalicylic acid, Aloxiprin, Ditazole, Clopidogrel, Dipyridamole, Epoprostenol, Eptifibatide, Indobufen, Prasugrel, Ticlopidine, Tirofiban, Treprostinil, Trifusal); Enzymes (e.g. Alteplase, Ancrod, Anistreplase, Fibrinolysin, Streptokinase, Tenecteplase, Urokinase); Direct thrombin inhibitors (e.g. Argatroban, Bivalirudin. Lepirudin, Melagatran, Ximelagratan); other antithrombotics (e.g. Dabigatran, Defibrotide, Dermatan sulfate, Fondaparinux, Rivaroxaban); antihypertensive drugs such as Diuretics (e.g. Bumetanide, Furosemide, Torsemide, Chlortalidone, Hydroclorothiazide, Chlorothiazide, Indapamide, metolaxone, Amiloride, Triamterene); Antiadrenergics (e.g. atenolol, metoprolol, oxprenolol, pindolol, propranolol, doxazosin, prazosin, teraxosin, labetalol); Calcium channel blockers (e.g. Amlodipine, felodipine, dsradipine, nifedipine, nimodipine, diltiazem, verapamil); Ace inhibitors (e.g. captopril, enalapril, fosinopril, lisinopril, perindopril, quinapril, ramipril, benzapril); Angiotensin II receptor antagonists (e.g. candesartan, irbesartan, losartan, telmisartan, valsartan); Aldosterone antagonist such as spironolactone; centrally acting adrenergic drugs (e.g. clonidine, guanabenz, methyldopa); antiarrhythmic drug of Class I that interfere with the sodium channel (e.g. quinidine, procainamide, disodyramide, lidocaine, mexiletine, tocamide, phenyloin, encamide, flecamide, moricizine, propafenone), Class II that are beta blockers (e.g. esmolol, propranolol, metoprolol); Class III that affect potassium efflux (e.g. amiodarone, azimilide, bretylium, clorilium, dofetilide, tedisamil, ibutilide, sematilide, sotalol); Class IV that affect the AV node (e.g. verapamil, diltiazem); Class V unknown mechanisms (e.g. adenoide, digoxin); antioxidant drugs such as Vitamin A, vitamin C, vitamin E, Coenzime Q10, melanonin, carotenoid terpenoids, non carotenoid terpenoids, flavonoid polyphenolic; antidepressants (e.g. mirtazapine, trazodone); antipsychotic drugs (e.g. fluphenazine, haloperidol, thiotixene, trifluoroperazine, loxapine, perphenazine, clozapine, quetiapine, risperidone, olanzapine); anxyolitics (Benzodiazepines such as diazepam, clonazepam, alprazolam, temazepam, chlordiazepoxide, flunitrazepam, lorazepam, clorazepam; Imidaxopyridines such as zolpidem, alpidem; Pyrazolopyrimidines such as zaleplon); antiemetic drugs such as Serotonine receptor antagonists (dolasetron, granisetron, ondansetron), dopamine antagonists (domperidone, droperidol, haloperidol, chlorpromazine, promethazine, metoclopramide) antihystamines (cyclizine, diphenydramine, dimenhydrinate, meclizine, promethazine, hydroxyzine); antiinfectives; antihystamines (e.g. mepyramine, antazoline, diphenihydramine, carbinoxamine, doxylamine, clemastine, dimethydrinate, cyclizine, chlorcyclizine, hydroxyzine, meclizine, promethazine, cyprotheptadine, azatidine, ketotifen, acrivastina, loratadine, terfenadine, cetrizidinem, azelastine, levocabastine, olopatadine, levocetrizine, desloratadine, fexofenadine, cromogli-
cate nedocromil, thiperamide, impromidine); antifungus (e.g. Nystatin, amphotericin B., natamycin, rimocidin, filipin, pimaricin, miconazole, ketoconazole, clotrimazole, econazole, mebendazole, bifonazole, oxiconazole, sertaconazole, sulconazole, tiaconazole, fluconazole, itraconazole, posaconazole, voriconazole, terbinafine, amorolfine, butenafine, anidulafungin, caspofungin, flucytosine, griseofulvin, fluocinonide) and antiviral drugs such as Anti-herpesvirus agents (e.g. Aciclovir, Cidofovir, Docosanol, Famciclovir, Fomivirsen, Foscarnet, Ganciclovir, Idoxuridine, Penciclovir, Trifluridine, Tromantadine, Valaciclovir, Valganciclovir, Vidarabine); Anti-influenza agents (Amantadine, Oseltamivir, Peramivir, Rimantadine, Zanamivir); Antiretroviral drugs (abacavir, didanosine, emtricitabine, lamivudine, stavudine, tenofovir, zalcitabine, zidovudine, adeforvir, tenofovir, efavirenz, delavirdine, nevirapine, amprenavir, atazanavir, darunavir, fosamprenavir, indinavir, lopinavir, nelfinavir, ritonavir, saquinavir, tipranavir); other antiviral agents (Enfuvirtide, Fomivirsen, Imiquimod, Inosine, Interferon, Podophyllotoxin, Ribavirin, Viramidine); drugs against neurological dysfunctions such as Parkinson's disease (e.g. dopamine agonists, L-dopa, Carbidopa, benzerazide, bromocriptine, pergolide, pramipexole, ropinipole, apomorphine, lisuride); drugs for the treatment of alcoholism (e.g. antabuse, naltrexone, vivitrol), and other addiction forms; vasodilators for the treatment of erectile dysfunction (e.g. Sildenafil, vardenafil, tadalafil), muscle relaxants (e.g. benzodiazepines, methocarbamol, baclofen, carisoprodol, chlorzoxazone, cyclobenzaprine, dantrolene, metaxalone, orphenadrine, tizanidine); muscle contractors; opioids; stimulating drugs (e.g. amphetamine, cocaina, caffeine, nicotine); tranquillizers; antibiotics such as macrolides; aminoglycosides; fluoroquinolones and β-lactames; vaccines; cytokines; growth factors; hormones including birth-control drugs; sympathomimetic drugs (e.g. amphetamine, benzylpiperazine, cathinone, chlorphentermine, clobenzolex, cocaine, cyclopentamine, ephedrine, fenfluramine, methylone, methylphenidate, Pemoline, phendimetrazine, phentermine, phenylephrine, propylhexedrine, pseudoephedrine, sibutramine, symephrine); diuretics; lipid regulator agents; antiandrogen agents (e.g. bicalutamide, cyproterone, flutamide, nilutamide); antiparasitics; blood thinners (e.g. warfarin); neoplastic drugs; antineoplastic drugs (e.g. chlorambucil, chloromethine, cyclophosphamide, melphalan, carmustine, fotemustine, lomustine, carboplatin, busulfan, dacarbazine, procarbazine, thioTEPA, uramustine, mechloretamine, methotrexate, cladribine, clofarabine, fludarabine, mercaptopurine, fluorouracil, vinblastine, vincristine, daunorubicin, epirubicin, bleomycin, hydroxyurea, alemtuzumar, cetuximab, aminolevulinic acid, altretamine, amsacrine, anagrelide, pentostatin, tretinoin); hypoglicaemics; nutritive and integrator agents; growth integrators; antienteric drugs; vaccines; antibodies; diagnosis and radio-opaque agents; or mixtures of the above mentioned drugs (e.g. combinations for the treatment of asthma containing steroids and β-agonists).

The above mentioned active ingredients are part of one or more structural classes, including, but not limited to, small molecules (preferably small insoluble molecules), peptides, polypeptides, proteins, polysaccharides, steroids, nucleotides, oligonucleotides, polynucleotides, fats, electrolytes and similar.

Specific examples include the $\beta_2$ agonists salbutamol, salmeterol (e.g. salmeterol xinafoate), formoterol and formoterol fumarate, fenoterol, carmoterol, indacaterol, corticosteroids such as beclomethasone dipropionate, budesonide, fluticasone (e.g. fluticasone dipropionate), mometasone (e.g. mometasone furoate) and ciclesonide. With respect to peptides and proteins, the present invention includes also the synthetic, recombinant, native, glycosilate and non glycosilate ones, biological active fragments and analogous.

Active ingredients for which an immediate release in the blood stream is particularly advantageous for a quick pharmacological effect include those to be used against migraine, nausea, insomnia, allergic reaction (including anaphylactic reactions), neurological and psychiatric disorders (in particular panic attacks and other psychosis or neurosis), erectile dysfunction, diabetes and related diseases, heart diseases, anticonvulsive drugs, bronchodilators and actives against pain and inflammation. According to the present invention vaccines made with antibodies, cells, corpuscles and cellular portions can also be administered.

The active ingredient can include two or more substances formulated together, for example one covered with the other, or one dispersed in a matrix of another substance, or a mixture of two or more active ingredients. Common examples of such formulations include active drugs covered with excipients, having the excipient the function of modifying the release rate or achieving the active ingredient targeting.

In the case of association of active ingredients, one of these can substitute partially or totally the soluble excipient becoming, besides active ingredient, a structural component of the solid particle. These cases are also part of the aim of the present invention. Examples of such substances are N-acetylcysteine and carbocysteine, having these suitable solubility, substantially low toxicity and perhaps mucolytic action.

Other examples of active substances are steroids and their salts, such as budesonide, testosterone, progesterone, flunisolide, triamcinolone, beclomethasone, betamethasone, dexamethasone, fluticasone, methylprednisolone, prednisone, hydrocortisone and similar; peptides such as cyclosporine and other water-insoluble peptides; retinoids such as cis-retinoic acid, 13-trans-retinoic acid and other derivatives of vitamin A and beta-carotene; vitamins D, E and K and other their precursors and water-insoluble derivatives; prostaglandins, leukotriens and their activators and inhibitors including prostacyclin, prostaglandins $E_1$ and $E_2$, tetrahydrocannabinol, pulmonary lipid surfactants; oil-soluble antioxidants; hydrophobic antibiotics and chemotherapic drugs such as amphotericin B, adriamycin and similar.

The soluble excipient or excipients of the pharmaceutical composition according to the invention usually have water solubility greater than 5 g/l and often greater than 100 g/l and more. They are preferably chosen among sugars, salts or aminoacids and have double function of minimizing the effect of the inhaled composition on the fluid's cellular outcome, and to stabilize the aqueous suspension obtained from the dry composition. Regarding the composition in its solid dry form, the excipient also forms the solid matrix in which the drug or active ingredient is dispersed. Examples of soluble excipients that may be used in the composition according to the invention are: alitame, acesulfame potassium, aspartame, saccharin, sodium saccharin, sodium cyclamate, sucralose, threalose, xylitol, citric acid, tartaric acid, cyclodextrins, dextrins, hydroxyethylcellulose, gelatine, malic acid, maltitol, maltodextrin, maltose, polydextrose, tartaric acid, sodium or potassium bicarbonate, sodium or potassium chloride, sodium or potassium citrate, phospholipids, lactose, sucrose, glucose, fructose, mannitol, sorbitol, natural aminoacids, alanine, glycine, serine, cysteine, phenylalanine, tyrosine, tryptophan, histidine, methionine, threonine, valine, isoleucine, leucine, arginine, lysine, aspartic acid, glutamic acid, asparagine, glutamine, proline, their salts and their possible simple chemical modifications such as in N-acetylcysteine and carbocysteine.

The preferred soluble excipients are alkaline metals salts such as sodium chloride or potassium chloride, and sugars, such as lactose.

As far as the hollow morphology of the particles is concerned, the composition requires the presence of a soluble excipient, preferably a sugar like lactose, able to form in the beginning of the solvent evaporation phase, during spray-drying, the backbone of the particle, producing therefore high porosity particles.

The surfactant of the pharmaceutical composition according to the invention can be chosen among different classes of surfactants of pharmaceutical use.

Surfactants suitable to be used in the present invention are all those substances characterized by medium or low molecular weight that contain a hydrophobic moiety, generally readily soluble in an organic solvent but weakly soluble or insoluble in water, and a hydrophilic (or polar) moiety, weakly soluble or insoluble in an organic solvent but readily soluble in water. Surfactants are classified according to their polar moiety. Therefore surfactant with a negatively charged polar moiety are called anionic surfactants, while cationic surfactants have a positively charged polar moiety. Uncharged surfactant are generally called non ionic, while surfactant charged both positively and negatively are called zwitterionic. Examples of anionic surfactants are salts of fatty acids (better known as soaps), sulphates, sulphate ethers and phosphate esters. Cationic surfactants are frequently based on polar groups containing amino groups. Most common non ionic surfactants are based on polar groups containing oligo-(ethylene-oxide) groups. Zwitterionic surfactants are generally characterized by a polar group formed by a quaternary amine and a sulphuric or carboxylic group.

Specific examples of this application are the following surfactants: benzalkonium chloride, cetrimide, docusate sodium, glyceryl monolaurate, sorbitan esters, sodium lauryl sulphate, polysorbates, phospholipids, biliary salts.

Non ionic surfactants, such as polysorbates and polyethylene and polyoxypropylene block copolymers, known as "Poloxamers", are preferred. Polysorbates are described in the CTFA International Cosmetic Ingredient Dictionary as mixtures of sorbitol and sorbitol anhydride fatty acid esters condensed with ethylene oxide. Particularly preferred are non ionic surfactants of the series known as "Tween", in particular the surfactant known as "Tween 80", a polyoxyethylensorbitan monolaurate available on the market.

The presence of a surfactant, and preferably of Tween 80, is necessary to reduce electrostatic charges found in formulations without it, the flow of the powder and the maintenance of the solid state in a homogeneous way without initial crystallization.

According to the present invention, phospholipids are not included in the above mentioned definition of surfactants or excipients.

As already indicated, the use of a sugar like lactose gives better results than phospholipids, that give with the same technique particles with a lower transition temperature and therefore more sensitive to humidity.

Also as far as their morphology is concerned, particles obtained with phospholipids show to be sensitive to the chosen evaporative parameters, having examples of porous particles obtained with collapse of the hollow structure of the original particle.

The dissolution rate of an inhalatory product reconstituted just before use must allow the patient to dissolve the same product preferably in less than 30 sec, even more preferably in less than 15 sec, in a necessary volume of liquid.

In this sense, even if the solubility of lactose in distilled water at room temperature is 20 g/100 ml, this solubility level is achievable only in a long time and heating the solution. Lactose, in fact, even if highly soluble, has a low dissolution rate.

It is preferred that solubilization of the product in water occurs at room temperature; it is therefore necessary to improve the solubilization of the formulation by reducing the particle size and promoting the dissolution through hollow morphology and surfactant in the formulation.

The dissolution rate is further improved if the solid state of the prevailing excipient is amorphous.

The dissolution time of particles having bulk density between 0.1 and 0.3 g/cc, mean particle size lower than 5 μm and internally hollow, according to the invention, is less than 15 seconds at room temperature in distilled water.

With respect to industrial manufacturing, a pharmaceutical product must be produced through a controlled, repeatable process, with high yield and consequently low cost.

The inhalatory formulation according to the invention can include a hydrophobic substance in order to reduce sensitivity to humidity. Such hydrophobic substance is preferably leucine, which makes the particle disaggregation easier.

In case of production of a solid product in powder form, this can occur using different techniques, well consolidated in the pharmaceutical industry.

The preparation of fine particles through spray-drying represents a preferred method according to the invention.

In case of industrial production, this technique is undoubtedly preferred to freeze-drying, which at the moment is the most expensive drying process, both for the apparatus used, and for the yield and production times. Further more, freeze-drying produces highly porous powders, which is not desired according to the present invention.

The pharmaceutical composition according to the invention can include other components, such as pH buffers and preservatives, but these are not generally necessary for the reason that the composition is stocked in solid dry state and that its related aqueous suspension is prepared extemporaneously just before use.

The term "solid dry composition" refers to a powder, granulate, tablet form composition or any other solid form with a humidity content that assures to the composition chemical stability in time. More precisely, the term "dry" refers to a solid composition with water content lower than 10% w/w, normally less than 5% and preferably less than 3%.

The amount of surfactant in the dry solid composition of the invention can change within a wide range. The surfactant and active ingredient weight ratio is preferably between 0.01 and 10.

The particle size of the dry solid composition of the invention is characterized by a mean diameter $X_{50}$ lower than 5 μm, preferably lower than 4 μm, more preferably between 1 and 3 μm.

The preparation process of the dry solid composition according to the invention includes the following operations of:

a) preparing a first phase (A) in which an active ingredient is in an appropriate liquid medium;
b) preparing a second phase (B) in which soluble excipients are dissolved and surfactants are dissolved or dispersed in an aqueous medium;
c) mixing said phases (A) and (B) to obtain a third phase (C) consisting of a homogeneous liquid medium;
d) drying said phase (C) in controlled conditions to obtain a dry powder with a mean particles size lower than 15 μm;
e) collecting said dry powder and stocking it in an appropriate way for an extemporaneous preparation of a suspension.

Phase (A) can be either a suspension of the active ingredient in an aqueous or non aqueous medium, or a solution of the active ingredient in an appropriate solvent.

It is preferable to prepare a solution, and to select the organic solvent among the water soluble ones. In this case, also phase (C) is a solution of all the components of the desired composition.

Instead, when phase (A) is a suspension of a hydrophobic active ingredient in an aqueous medium, also phase (C) is a suspension in an aqueous medium that will dissolve the soluble components such as excipients and surfactants.

Operation d) consists of eliminating the liquid, dissolving or dispersing medium, from phase (C), in order to obtain a dry powder with desired dimensional features. Such drying is preferably obtained by spray-drying. The features of the nozzle and the process parameters are chosen in order to dry out the liquid medium from the solution or suspension (C) and to obtain a powder with desired particle size.

The powder obtained is then stocked as such or formulated in tablets or other suitable form. The relatively high particle size of the dry composition according to the invention is particularly advantageous for different reasons. As already said before, coarse particles have a lower tendency to aggregate than fine particles. Furthermore, the yield of the spray-drying process can be higher than the one of commercial known processes used to produce correspondent fine dry-state inhalation particles. At last, the collection and manipulation of the powders is easier.

The dry solid pharmaceutical composition described above is intended to be inhaled as such or to be used to prepare a stable extemporaneous suspension or solution of the drug or active ingredient in an appropriate volume of dispersing liquid, preferably water or physiological solution.

According to an aspect of the present invention, the dry solid pharmaceutical composition described above is used to prepare a stable extemporaneous suspension or solution of the drug or active ingredient in an appropriate volume of water or physiological solution.

As known in the field, an extemporaneous preparation is a preparation completed just before use, which means right before the administration of the drug to the patient. In the present description, the term "extemporaneous preparation" also includes a preparation carried out by a pharmacist and intended to be used by the patient in a relatively short period of time from such preparation. More in general, the term "extemporaneous preparation" refers to all those cases in which the solution or suspension is not directly produced by the pharmaceutical industry and commercialized in a ready to be used form, but is prepared in a moment that follows the preparation of the dry solid composition, usually in a moment close to the administration to the patient.

The concept of extemporaneous preparation is also extended to the preparation of a solution by bringing the dry composition in contact with the liquid, inside a delivery device.

The administration of a powder obtained according to the invention can be achieved through:

Dry powder inhaler
Nebulizer
Pressurized inhaler
Non pressurized inhaler, soft-mist kind The inhalation powder according to the invention includes particles with a bulk density lower than 0.3 g/cc. Preferably, such bulk density is lower than 0.2 g/cc and their particle size is such that the mean diameter of at least 50% of the particles is lower than 5 μm.

In case of administration through a nebulizer, the composition (with excipient and surfactant) must not influence negatively the qualitative and quantitative delivery of the product.

In case of nebulizers, these are found to be assembled according to different functioning mechanisms.

These include:
Pneumatic nebulizers
Ultrasound nebulizers
Mesh or soft-mist nebulizers The invention proposes to make the use of these nebulizers more efficient and versatile, through the used formulation.

The obtained results show that combining a soluble excipient and a surfactant it is possible to achieve better formulations than the ones with just buffer or just water.

Solutions of the drug in saline buffer or similar carriers are commonly used to generate an aerosol in a nebulizer. Inside the ampoule of a conventional air nebulizer, there is a small unit that produces aerosolized droplets. The walls of the ampoule work as deflectors, removing large droplets from the aerosol. Large droplets run along the walls and fall back in the cup leaving a mist of small droplets that can penetrate in the lungs. An air or oxygen flow carries the aerosol across the nebulizer mouthpiece.

Most common nebulizers operate according to Bernoulli's theory and make use of an air or oxygen flow to generate spray particles. More sophisticated nebulizers make use of ultrasounds or vibrating piezoelectric parts to generate spray particles. Both types are known in the field and are described in the pharmaceutical literature.

Since all nebulizers require a liquid medium for the development of the aerosol spray and since the spray must be directly inhaled in the lungs, water is the most suitable medium to be used. A problem occurs when the drug is itself not sufficiently stable in water in order to assure long stability to the aqueous formulation.

An alternative to refrigerate the solution or suspension that has been already prepared is to prepare the medicamentous solution immediately before use.

The pulmonary administration of drugs is developed through the characterization of formulations delivered from a device to a liquid or dry impinger and defining the FPF (Fine Particle Fraction), that is the amount of drug having an aerodynamic diameter lower than 5 μm. This parameter does not provide information about the amount of drug deposited in the alveoli or bronchi, being well known that bronchodilators don't give real benefit when deposited in the alveoli.

In this sense, if we consider the percentage of deposition in the Stages 4 and 5 of a Multi Stage liquid Impinger working at 30 lpm, the sum of Stage 4=40% and Stage 5=20%, is equivalent to the sum of Stage 4=20% and Stage 5=40%, but, potentially, with two different pharmacological effects between the two products.

Such differences would be easily found using different nebulizer with the same formulation. The presented invention proposes therefore a new technological approach capable, after manipulation of the formulation, to optimize inhalatory administration of a drug with a nebulizer or a soft-mist device, in the following ways:
quantitative: larger amounts of drug delivered over time
qualitative: delivery of finer droplets
pre-definition of the nebulized droplet size based on the lung targeting
improvement of long term stability of the product The appropriate combination, according to the formulator's needs, can allow the production of formulations having desired dimensional distribution depending on the nebulizer or therapy.

In this way it should theoretically be possible to obtain an inhalatory product with a fine particle size, for preferential lung deposition, and coarser particle size, for a bronchial or central deposition, without modifying the device or without needing two different nebulizers for two different inhalatory practices.

The solid state product can consist of one or more unitary doses of the medicine and a correspondent volume of a dispersing medium.

In another configuration of the product, the drug alone can be stocked in solid state and the dispersing mean could include suitable amounts of polysaccharide and surfactant.

The formulations realized as examples show that through a suitable formulation it is possible to optimize:
the amount of drug delivered from the device
the nebulized droplets' size
the amount deposited in the respiratory tract The formulation can be delivered from a common nebulizer or a soft-mist device.

According to an aspect of the invention, a kit for the administration of the drug in powder form, in case of the patient's need, or, if possible, its dispersion in water and easy transfer in a nebulization ampoule, consists of a device including the required components in dosed amounts. Such device is configured as a glass or plastic tube shown in FIG. 8, where different operative positions marked with A through E are listed. The delivery device according to the invention substantially consists of a tube (10) divided into two compartments (12, 14), of two rubber or plastic seals (15, 17), able to slide along the tube applying a pressure through an external piston (18). The tube (10) is provided with a by-pass obtained enlarging (20) the side section of the tube itself. The upper compartment (12) contains the powder state inhalatory formulation, while the lower compartment (14) contains an appropriate dose of liquid, enough to completely disperse the powder (22), which can be in single or multiple dosages.

Figure 5:
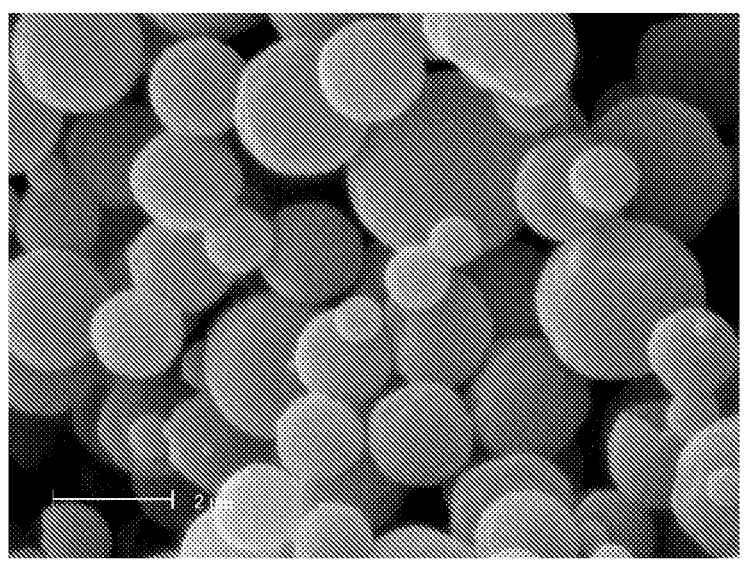
FIG. 5 is an electron microscope photograph of the particles from example 24.
Figure 6:
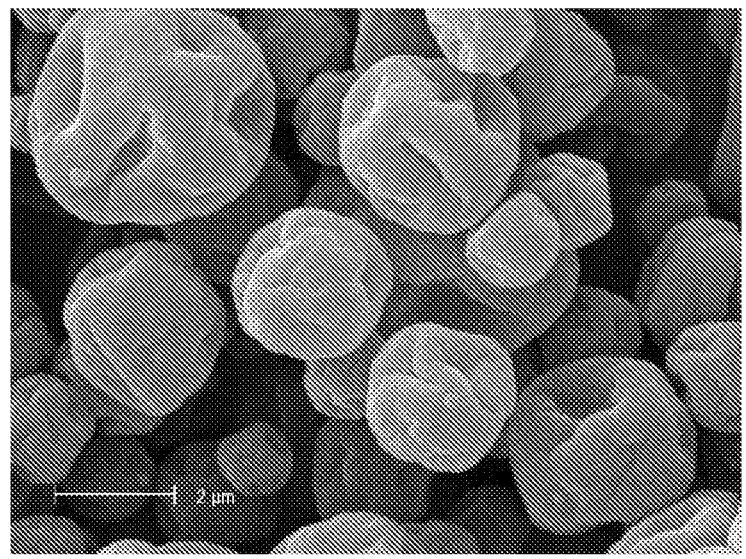
FIG. 6 is an electron microscope photograph of the particles from example 25.
Figure 7:
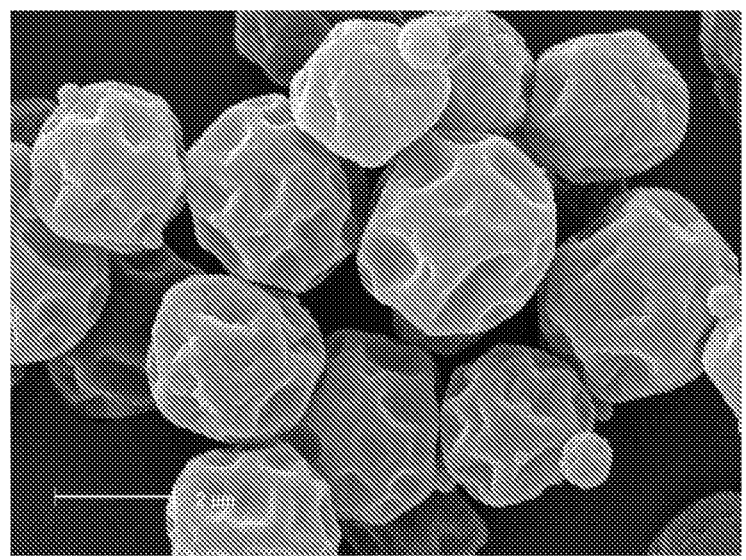
FIG. 7 is an electron microscope photograph of the particles from example 26.

The tube is closed on the top with common pharmaceutical use packaging material (e.g. aluminium), to form a piercable seal (26). In case of delivery of powder, the seal (26) is pierced with a mouthpiece (28) provided with a piercing rod (30), which circumscribes a central tube for the delivery of the powder, as shown in FIG. 8B. FIG. 9A shows the mouthpiece (28) in elevation position, and shows that it's provided of a series of small holes (32), for the inlet of air in the vial. FIG. 9B shows the mouthpiece (28) in section from the top. In case of administration of a liquid, the piston (18) moves the lower seal 17 towards the top, moving the liquid through the by-pass in the upper compartment to mix with and dissolve the powder (FIG. 5C). The seal is therefore pierced with a thinner dosing rod (30), included in a mouthpiece (28), for a fine dosage, and the dose is delivered applying further pressure, as in a syringe (FIG. 8E). FIGS. 10A and 10B show the mouthpiece (28) respectively from elevated position and in section from the top.

Demonstration of the Particle Size of the Nebulized Product

To demonstrate that the nebulized product delivered from four conventional nebulizers available on the market, with different working mechanisms, indicated in following as M, A, C and N, respectively:

M, A: nebulizer provided with a mesh or a piezoelectric device
C: pneumatic nebulizer (jet nebulizer)
N: ultrasonic nebulizer has improved in relation to the droplet diameter of the nebulized product and/or to the dose delivered in a standard delivery time for a patient, correspondent to 5 minutes, we have dispersed in 2 ml of distilled water 40 mg of powder, produced according to example 4 later described, correspondent to a 240 μg dose of salbutamol, comparing it with an equivalent dose of salbutamol sulphate dissolved in 2 ml of distilled water.

The 2 ml of solution of the two compositions taken in consideration have been loaded in the 4 nebulizers and these have been activated for 5 minutes to measure the delivered amount without forced inhalation.

The same formulation has been investigated measuring after the first minute of continuous delivery the dimensional distribution of the delivered droplets, by putting the device in front of a laser ray of a light scattering particle size analyzer, Sympatec Helos, provided of a R1 measuring lens for the range 0.1-35 μm.

The results shown in the following table show an improvement of one or both of the measured parameters for all of the investigated nebulizers, showing that the formulation is practically independent from the atomization type.

|   | Example. 4 | | Salbutamol sulphate | |
|---|---|---|---|---|
|   | Delivered dose (%) | $X_{50}$ (μm) | Delivered dose (%) | $X_{50}$ (μm) |
| M | 51.3 | 5.94 | 14.1 | 10.17 |
| A | 24.1 | 5.13 | 26.1 | 8.21 |
| C | 75.3 | 7.18 | 56.7 | 8.67 |
| N | 83.3 | 6.11 | 58.5 | 6.52 |

Demonstration of the Preferential Drug Targeting

In our case you can indicate we are able to modify the pulmonary deposition in the deep lung of particle size lower than 5 μm, if referred to the deposition achieved with a saline solution or suspension of 5 common inhalation drugs.

Calculation of the Number of Particles that can Reach the Deep Lung

If we consider a dose of dry powder for inhalation of 100 μg constituted of monodispersed spherical particles with density 1 g/cc and with geometric diameter 2 μm, the number (n) of particles present in this mass of powder can be calculated from the following equation:

$$n = \frac{m}{DV_i} \quad (1)$$

where:
D=density of the bulk of powder
m=mass of powder
$V_i$=volume of the individual particle
n=number of particles If we consider a particle with geometric diameter equal to 2 μm as described above, its individual volume $V_i$ can be calculated from the following equation:

$$V_i = \frac{d^3 \pi}{6} = 4.19 \text{ μm}^3 \quad (2)$$

If:
m=100 μg
Vi=4.19 μm³
D=1 g/cc equivalent to $10^{-6}$ μg/μm³
n would be equivalent to $2.38 \times 10^7$ particles.

A reduction of the diameter of the particles from 2 μm to 1 μm would result in a $V_i$ equivalent to 0.52 μm³, thus increasing the number of particles for the 100 μg described to $1.92 \times 10^8$.

Assuming that the 2 μm powder for which the estimated theoretical number n of particles is delivered to the respirable region of a human lung with an efficiency comparable to the one achievable with common dry powder inhalers available on the market (approximately 20%), the actual respirable dose is equal to n/5 or $4.76 \times 10^6$.

The theoretical lung surface area covered by this respirable dose can be calculated starting from the number of particles delivered to the lung and the projected area A on a plane of a sphere with equivalent diameter to the particle. In this case:

$$A = \frac{\pi}{4} d^2 = 3.14 \text{ μm}^2 \quad (3)$$

This individual area A must then be multiplied by the number of particles delivered to the respirable region n:

$$A_{tot} = A \times n = 4.76 \times 10^6 \times 3.14 = 1.49 \times 10^7 \text{ μm}^2 \approx 0.15 \text{ cm}^2 \quad (4)$$

Using the same procedure to calculate the area covered by 1 μm particles with the same lung deposition efficiency this would be:

$$= 3.84 \times 10^7 \times 0.78 = 2.99 \times 10^7 \text{ μm}^2 \approx 0.30 \text{ cm}^2$$

A fractionation of the dose in smaller particles with half the geometric diameter of the previous ones increases by approximately 8 times the number of particles delivered to the respirable region but would lead to a coating of the lung area that is only doubled.

If we consider now the case of dry powder particles obtained by formulation of active drug and excipient with a common technique like spray drying in which the drug represents just 1% of the total mass of particle, this would mean that a dose of 100 μg of drug would have to be delivered in a 10 mg dose of powder.

If we still consider monodispersed spherical particles with dg=2 μm the number n of particles would be calculated according to equation (1) and will be equal to $2.38 \times 10^9$ particles, and $1.92 \times 10^{10}$ particles in the case of dg=1.

In both cases if the deposition efficiency remains 20%, the same respirable dose will cover a surface area 100 times larger than the one calculated earlier according to equation (4).

$$\text{Or: } = 4.76 \times 10^8 \times 3.14 = 1.49 \times 10^9 \text{ m}^2 = 15 \text{ cm}^2$$

$$\text{and } = 3.84 \times 10^9 \times 0.78 = 2.99 \times 10^9 \text{ μm}^2 \approx 30 \text{ cm}^2$$

Manipulations of the dilution of the drug within an excipient matrix from 1% in loading to 0.1% or lower and increases in respirability of the powder from 20% to achievable levels of 50% or even 70% lead to deposition areas of 750 cm² (dg=1 μm; 0.1% drug loading; 50% respirable fraction of the dose). Such deposition area lead to more predictable effects and better control in therapy.

In consideration of the fact that an ideal reduction of the particle size to less than 1 μm is very difficult to achieve, especially for dry powder particles, the dispersion of the drug in an excipient matrix represents a reasonable approach that also optimizes lung deposition and particle-particle interactions. The active drug can be dispersed in a pre-engineered excipient matrix with desirable characteristics in which the active drug does not provide any potentially negative effect.

It has been interestingly found that the technological approach of diluting a drug within an excipient matrix as to form a dry particle for inhalation can be better utilized with certain specific types of formulations for inhalation.

If we consider a dose of 100 μg of drug this can be formulated according to 3 different technological approaches that lead to dry powder particles with theoretical aerodynamic diameter of 2 μm.

Dense particles (theoeretical density of about 1 g/cc)
Light particles (theoretical density of about <0.1 g/cc)
Intermediate density particles (theoretical density between 0.1 and 1 g/cc)

Considering the formula that correlates geometric diameter ($d_g$) and aerodynamic diameter ($d_{ae}$) through their density ($\rho$)

$$d_{ae} = d_g \times \sqrt{\rho} \qquad (5)$$

the characteristics of particles presented in the table here below are illustrative examples of dense, light and intermediate dry particles:

| | Type | $d_g$ (μm) | $d_{ae}$ (μm) | $\rho$ (g/cc) |
|---|---|---|---|---|
| A | Dense | 2.0 | 2.0 | 1.0 |
| B | Light | 10.0 | 2.0 | 0.04 |
| C | Intermediate | 3.0 | 2.0 | 0.44 |

In the case of types B and C formulations obtained by spray drying starting at a drug loading in the composition of 0.4%, the powder dose to deliver correspond to 25 mg. If the powder composition consists of monodispersed particles with spherical morphology corresponding to the dg presented in the table above, it is possible to calculate the number of particles in which the powder dose is subdivided utilizing the density parameter presented in the table.

| | Type | Dose of powder (mg) | Powder volume (μm$^3$) | $\rho$ (g/cc) | Number of particles |
|---|---|---|---|---|---|
| A | Dense | 0.1 | $1 \times 10^8$ | 1.0 | $2.38 \times 10^7$ |
| B | Light | 25.0 | $6.25 \times 10^{11}$ | 0.04 | $1.2 \times 10^9$ |
| C | Intermediate | 25.0 | $5.63 \times 10^{10}$ | 0.44 | $4.0 \times 10^9$ |

Assuming that a reasonable deposition efficiency at the lung target site is of about 50%, we can calculate the theoretical number of particles delivered to the target and the corresponding surface area of deposition according to equations (3) and (4).

| | Type | Number of particles at target | Particle area (μm$^2$) | Deposition area (cm$^2$) |
|---|---|---|---|---|
| A | Dense | $1.19 \times 10^7$ | 3.14 | 0.37 |
| B | Light | $6.0 \times 10^8$ | 15.7 | 94.2 |
| C | Intermediate | $2.0 \times 10^9$ | 4.71 | 94.2 |

The calculation shows that in theoretical terms the dilution of the drug within an excipient matrix can be advantageous as it leads to an increase of the deposition area reached by the drug.

It is also interesting to notice that in this calculation the simulation of dry powders with intermediate and light density leads to an equivalent value of deposition area, thus indicating that either one of the two technological approaches is feasible from a therapeutic point of view.

In general, the use of diluted inhalatory formulations is preferred in the case of local and systemic therapy via the lungs.

In the case of local therapies like the one with bronchodilators, it is important to notice that these drugs have really high potency, i.e. their therapeutic dose is sometimes in the order of very few micrograms as the case for formoterol (12 μg single dose) or carmoterol (1 μg single dose). The target for these drugs is represented by the bronchial region constituted by smooth muscle cells. The literature reports that the concentration of β2 receptors (the target for bronchodilator drugs) on a single smooth muscle cell has been calculated to be in the order of 30 to 40.000 receptors per cell. It is clear that such an elevated number of targets masks very well the inefficiency of current inhalatory formulations. An increase in lung deposition efficiency expressed in terms of amount of drug delivered and also of surface area covered can lead to a more efficient use of bronchodilators at drug doses significantly lower than the current ones.

A similar dilution approach can clearly also be utilized in the case of pulmonary administration to the alveolar region as in the case of anti-inflammatory corticosteroid or in the case of systemic therapies. In this case the reference point is represented by the number of alveoli present in the lung which has been measured around 480 millions (range 274 to 790 millions) thus comparable to the administration of a diluted dry powder formulation.

If we consider the comparison of light and intermediate dry powder formulations as ideal compositions for lung delivery it is very important to keep into account the fact that the use of dry powders with low density as in the two cases generally requires the use of single dose inhalers like the Aerolizer® or Turbospin®.

In the case of the Aerolizer®, the device utilizes a gelatin capsule of size #3 with an internal volume of 0.3 ml.

Similarly in the case of Turbospin®, the gelatine capsule utilized is size #2 with internal volume of 0.37 ml.

It is generally recommended to fill only up to 50% of the internal available volume of gelatin capsules intended for inhalation.

The use of formulations with very low density can thus represent an important limiting factor when these powders, as described by Tarara et. Al (US 2005/0074498A1), present most preferred bulk densities lower than 0.05 g/cm$^3$.

In the case of a very light dry powder with bulk density of 0.04 g/cc, as described above to exemplify a light particle formulations, it would be possible to fill only 6 and 7.4 mg in gelatine capsules of #3 and #2 size. This represents a serious limiting factor since multiple administrations will have to be performed in the case of insufficient filling volume in the capsule when large amount of drugs have to be delivered.

Interestingly, the authors of previous literature never evaluated both bulk and tapped density of their inhalation powders, but disregarded one or the other in their work.

Tarara et al. (US 2005/0074498A1) indicated bulk density as the relevant parameter for light dry powders for inhalation with a preferred bulk density of less than 0.1 g/cc.

Edwards et al (U.S. Pat. No. 5,874,064), on the other end, indicated tapped density as the main parameter for their aerodynamically light powders and setting their limit to 0.4 g/cc.

Pilcer et al (Pharm. Res. Vol. 23, No. 5, May 2006, pp. 931-940) produced dry powder formulations by spray drying starting from a liquid suspension of micronized drug which is coated with lipids to increase flowability of the powder and aerosolization.

The formulations presented by Pilcer show values for bulk density ($d_b$) and tapped density ($d_t$) whose ratio ($d_b/d_t$) is comprised between 0.64 and 0.73, which is not very far from a formulation of pure spray dried active drug (0.76). Based on the preparation technique these powders resulted with internally dense structure and do not present significant compactability properties as indicated by the high values of $d_b/d_t$.

We have found that it is alternatively possible to produce dry powder particles with low particle size ($X_{50}$<5 m) with $d_b$ comprised in the range 0.1-0.3 g/cc and $d_t$ in the range 0.15-0.7 g/cc, and characterized by ratios $d_b/d_t$ comprised within the range 0.2-0.65 and with the property of being able to be partitioned at large masses in small volumes still retaining their aerodynamic properties.

The bulk density ($d_b$) of a bulk of powder can be determined according to the European Pharmacopoeia (Ph. Eur.) by measuring the volume of a known mass of powder that has been passed through a screen into a graduated cylinder.

Similarly the European Pharmacopoeia indicates that tapped density ($d_t$) of a bulk of powder is achieved by mechanically tapping a measuring cylinder containing a powder sample. After observing the initial volume, the cylinder is mechanically tapped, and volume readings are taken until little further volume change is observed.

Based on the rationale explained above, in the case of specific formulations in which the active drug has been diluted within an excipient matrix as in the case of spray dried particles, it is possible to calculate the number of particles that are capable to reach the deep lung (dae<5.0 μm).

This calculation is possible knowing certain factors:
Diameter of the particle
Density of the particle
Fine Particle Fraction
Dilution factor of the drug in the powder expressed as the ratio of the mass of powder divided by the mass of active drug in the powder It is reasonable to expect that drug dosages in the range starting from less than 0.1 g up to 100 μg would be diluted to the point where the dose of powder is comprised within the range 0.5-50 mg.

Similarly a dose of active in the range 100 μg-1 mg will be converted in a dose of powder in the range 1.18-50 mg.

A dose of active in the range 1-10 mg will be converted in a dose of powder in the range 11.8-50 mg.

A dose of active in the range 10-100 mg will be converted in a dose of powder in the range 118-500 mg.

A dose of active in the range 100 mg-1.0 g will be converted in a dose of powder in the range 1.18 g-5.0 g.

Assuming that the powders produced will have diameter in the range 0.1 μm-5.0 μm, a Fine Particle Fraction (FPF<5.0 μm) between 35% and 80% of the initial dose and that the powder tapped density ($d_t$—equivalent to the envelope density of the particle) is within the range 0.15-0.70 g/cc it is possible to calculate using equations (1) and (2) the number of particles in a given dose of powder and by multiplying this for FPF, a range of Fine Particle Doses for each formulation not just in terms of mass of drug deposited, as in conventional methods, but in terms of number of particles as presented in the table here below.

| Dose range | Dose of powder | Dilution factor | Particle size (μm) | $d_t$ (g/cc) | FPF | Range of No. of particles |
|---|---|---|---|---|---|---|
| <1 μg | 0.5-50 mg | 5.000-500.000 | 0.1-5.0 | 0.15-0.7 | 0.35-0.80 | $3.8 \times 10^6$-$5.1 \times 10^{11}$ |
| 1-10 μg | 0.5-50 mg | 50-50.000 | 0.1-5.0 | 0.15-0.7 | 0.35-0.80 | $3.8 \times 10^6$-$5.1 \times 10^{11}$ |
| 10-100 μg | 0.5-50 mg | 5-5.000 | 0.1-5.0 | 0.15-0.7 | 0.35-0.80 | $3.8 \times 10^6$-$5.1 \times 10^{11}$ |
| 100 μg-1 mg | 1.18-50 mg | 1.18-500 | 0.1-5.0 | 0.15-0.7 | 0.35-0.80 | $9.0 \times 10^6$-$5.1 \times 10^{11}$ |
| 1 mg-10 mg | 11.8-50 mg | 1.18-50 | 0.1-5.0 | 0.15-0.7 | 0.35-0.80 | $9.0 \times 10^7$-$5.1 \times 10^{11}$ |
| 10 mg-100 mg | 118-500 mg | 1.18-50 | 0.1-5.0 | 0.15-0.7 | 0.35-0.80 | $9.0 \times 10^8$-$5.1 \times 10^{12}$ |
| 100 mg-1 g | 1.18-5 g | 1.18-50 | 0.1-5.0 | 0.15-0.7 | 0.35-0.80 | $9.0 \times 10^9$-$5.1 \times 10^{13}$ |

The invention will be now be illustrated with reference to the following non-limiting examples.

EXAMPLES

Preparation of the Solid Dry Composition

TABLE 1

| Example | Composition | Surfactant/active | $X_{50}$ (μm) | Bulk density $d_b$ (g/cc) | Tapped density $d_t$ (g/cc) | $d_b/d_t$ |
|---|---|---|---|---|---|---|
| 1 | Budesonide 1.0% Formoterol Fumarate 0.05% Lactose 96.95% Tween 80 2% | 1.90 | 2.51 | 0.16 | 0.26 | 0.61 |
| 2 | Budesonide 1.0% Formoterol Fumarate 0.05% Lactose 96.95% Tween 80 2% | 1.90 | 2.45 | 0.15 | 0.25 | 0.60 |
| 3 | Salbutamol sulphate 0.3% Lactose 99.0% Tween 80 0.7% | 2.33 | 2.41 | 0.10 | 0.17 | 0.59 |

TABLE 1-continued

| Example | Composition | Surfactant/active | $X_{50}$ (μm) | Bulk density $d_b$ (g/cc) | Tapped density $d_t$ (g/cc) | $d_b/d_t$ |
|---|---|---|---|---|---|---|
| 4 | Salbutamol sulphate 0.6%<br>Lactose 98.0%<br>Tween 80 1.4% | 2.33 | 4.20 | 0.13 | 0.25 | 0.52 |
| 5 | Formoterol fumarate 0.03%<br>Tween 80 0.07%<br>Lactose 99.9% | 2.33 | 2.64 | 0.18 | 0.28 | 0.64 |
| 6 | BDP 0.5%<br>Tween 20 1.0%<br>Span 20 0.2%<br>NaCl 11.25%<br>Lactose 87.05% | 2.40 | 2.70 | 0.11 | 0.24 | 0.45 |
| 7 | Budesonide 1.0%<br>Tween 80 2.0%<br>Lactose 97.0% | 2.0 | 2.89 | 0.19 | 0.30 | 0.64 |
| 8 | Budesonide 1.0%<br>Salbutamol sulphate 2.5%<br>Tween 80 2.0%<br>Lactose 94.5% | 0.57 | 2.50 | 0.19 | 0.31 | 0.61 |
| 9 | BDP 0.5%<br>Salbutamol sulphate 1.2%<br>Tween 20 1.0%<br>Span 20 0.2%<br>NaCl 11.25%<br>Lactose 85.85% | 0.70 | 2.91 | 0.10 | 0.23 | 0.43 |
| 10 | Salbutamol sulphate 2.5%<br>Tween 80 2.0%<br>Lactose 95.5% | 0.80 | 2.89 | 0.14 | 0.24 | 0.58 |
| 11 | Ceftazidime 48.1%<br>Tween 80 9.6%<br>Lactose 42.3% | 0.20 | 3.37 | 0.20 | 0.66 | 0.30 |
| 12 | BDP 0.5%<br>Tween 20 1.0%<br>Span 20 0.2%<br>NaCl 11.25%<br>Lactose 87.05% | 2.40 | 3.53 | 0.12 | 0.23 | 0.52 |
| 13 | Budesonide 1.0%<br>Tween 80 2.0%<br>Lactose 97.0% | 2 | 2.97 | 0.15 | 0.25 | 0.60 |
| 14 | Budesonide 1.0%<br>Tween 80 2.0%<br>Maltodextrin 97.0% | 2 | 3.96 | 0.12 | 0.25 | 0.46 |
| 15 | Budesonide 2.0%<br>Tween 80 0.5%<br>L-Leucine 10%<br>Lactose 87.5% | 0.25 | 2.48 | 0.12 | 0.23 | 0.52 |
| 16 | Budesonide 1.0%<br>Tween 80 0.5%<br>L-Leucine 10%<br>Lactose 88.5% | 0.50 | 2.39 | 0.14 | 0.27 | 0.52 |
| 17 | Formoterol fumarate 0.08%<br>Tween 80 0.5%<br>L-Leucine 15%<br>Lactose 84.42% | 6.25 | 2.44 | 0.16 | 0.43 | 0.37 |
| 18 | Formoterol fumarate 0.08%<br>Tween 80 0.5%<br>L-Leucine 30%<br>Lactose 69.42% | 6.25 | 2.64 | 0.10 | 0.24 | 0.43 |
| 19 | Insulin 10%<br>Tween 80 0.5%<br>L-Leucine 10%<br>Lactose 79.5% | 0.05 | 3.23 | 0.18 | 0.56 | 0.32 |
| 20 | Insulin 3.5%<br>Tween 80 0.5%<br>L-Leucine 10%<br>Lactose 86% | 0.143 | 2.32 | 0.20 | 0.58 | 0.34 |
| 21 | Ceftazidime 50%<br>Tween 80 0.5%<br>L-Leucine 15%<br>Lactose 34.5% | 0.01 | 2.96 | 0.32 | 0.75 | 0.43 |
| 22 | Colistine 40%<br>Tween 80 0.4%<br>L-Leucine 15%<br>Lactose 44.6% | 0.01 | 2.98 | 0.15 | 0.42 | 0.36 |

TABLE 1-continued

| | | | | composition | | | |
|---|---|---|---|---|---|---|---|
| Example | Composition | Surfactant/active | $X_{50}$ (μm) | Bulk density $d_b$ (g/cc) | Tapped density $d_t$ (g/cc) | $d_b/d_t$ | |
| 23 | Ceftazidime 40%<br>Tween 80 0.4%<br>L-Leucine 30%<br>Lactose 29.6% | 0.01 | 2.96 | 0.22 | 0.70 | 0.31 | |
| 24 | Ceftazidime 20%<br>Tween 80 0.5%<br>L-Leucine 15%<br>Lactose 64.5% | 0.025 | 2.41 | 0.21 | 0.62 | 0.34 | |
| 25 | Ceftazidime 79.2%<br>L-Leucine 20.0%<br>Tween 80 0.8% | 0.01 | 2.90 | 0.26 | 0.67 | 0.39 | |
| 26 | Ceftazidime 84.1%<br>L-Leucine 15.0%<br>Tween 80 0.9% | 0.01 | 3.37 | 0.29 | 0.70 | 0.41 | |

The compositions of example 14, 18, 21, 22, 24, 25, 26 have been characterized morphologically. They are made of particles with a substantial spherical shape and internally hollow morphology, as shown in the FIGS. 1-7, which are images of the dry powder at different enlargements.

TABLE 2

| | | preparation | | |
|---|---|---|---|---|
| Example | Active ingredient | Composition (g) | Preparation method | Operative conditions |
| 1 | Budesonide<br>Formoterol fumarate | Budesonide 0.75<br>Formoterol fumarate 0.0375<br>Lactose 72.71<br>Tween 80 1.5 | Spray drying | Solvent: water/ethanol 70/30<br>Conc. Solids: 5% weight/vol<br>Spray temperature: 120° C.<br>Feed flow: 3 ml/min<br>Nozzle diameter: 0.5 mm<br>Volume dried: 1500 ml |
| 2 | Budesonide<br>Formoterol fumarate | Budesonide 0.25<br>Formoterol fumarate 0.0125<br>Lactose 24.24<br>Tween 80 0.5 | Spray drying | Solvent: water/ethanol 70/30<br>Conc. Solids: 5% weight/vol<br>Spray temperature: 120° C.<br>Feed flow: 3 ml/min<br>Nozzle diameter: 0.5 mm<br>Volume dried: 500 ml |
| 3 | Salbutamol Sulphate | Salbutamol Sulphate 0.075<br>Lactose 24.75<br>Tween 80 0.175 | Spray drying | Solvent: water<br>Conc. Solids: 5% weight/vol<br>Spray temperature: 130° C.<br>Feed flow: 3 ml/min<br>Nozzle diameter: 0.5<br>Volume dried: 500 ml |
| 4 | Salbutamol Sulphate | Salbutamol Sulphate 0.15<br>Lactose 24.5<br>Tween 80 0.35 | Spray drying | Solvent: water<br>Conc. Solids: 5% weight/vol<br>Spray temperature: 130° C.<br>Feed flow: 3 ml/min<br>Nozzle diameter: 0.5<br>Volume dried: 500 ml |
| 5 | Formoterol fumarate | Formoterol fumarate 0.015<br>Lactose 49.95<br>Tween 80 0.035 | Spray drying | Solvent: water/ethanol 70/30<br>Conc. Solids: 5% weight/vol<br>Spray temperature: 120° C.<br>Feed flow: 3 ml/min<br>Nozzle diameter: 0.5 mm<br>Volume dried: 1000 ml |
| 6 | BDP | BDP 0.05<br>Lactose 8.705<br>NaCl 1.125<br>Tween 20 0.1<br>Span 20 0.02 | Spray drying | Solvent: water/ethanol 30/70<br>Conc. Solids: 1% weight/vol<br>Spray temperature: 130° C.<br>Feed flow: 5 ml/min<br>Nozzle diameter: 0.5<br>Volume dried: 1000 ml |
| 7 | Budesonide | Budesonide 0.5<br>Lactose 48.5<br>Tween 80 1 | Spray drying | Solvent: water/ethanol 70/30<br>Conc. Solids: 5% weight/vol<br>Spray temperature: 120° C.<br>Feed flow: 3 ml/min<br>Nozzle diameter: 0.5 mm<br>Volume dried: 1000 ml |

TABLE 2-continued preparation

| Example | Active ingredient | Composition (g) | Preparation method | Operative conditions |
|---|---|---|---|---|
| 8 | Budesonide Salbutamol Sulphate | Budesonide 0.5<br>Salbutamol Sulphate 1.25<br>Lactose 47.25<br>Tween 80 1 | Spray drying | Solvent: water/ethanol 70/30<br>Conc. Solids: 5% weight/vol<br>Spray temperature: 120° C.<br>Feed flow: 3 ml/min<br>Nozzle diameter: 0.5 mm<br>Volume dried: 1000 ml |
| 9 | BDP Salbutamol Sulphate | BDP 0.05<br>Salbutamol Sulphate 0.12<br>Lactose 8.585<br>NaCl 1.125<br>Tween 20 0.1<br>Span 20 0.02 | Spray drying | Solvent: water/ethanol 30/70<br>Conc. Solids: 1% weight/vol<br>Spray temperature: 130° C.<br>Feed flow: 5 ml/min<br>Nozzle diameter: 0.5<br>Volume dried: 1000 ml |
| 10 | Salbutamol Sulphate | Salbutamol Sulphate 0.625<br>Lactose 23.875<br>Tween 80 0.5 | Spray drying | Solvent: water/ethanol 70/30<br>Conc. Solids: 5% weight/vol<br>Spray temperature: 130° C.<br>Feed flow: 3 ml/min<br>Nozzle diameter: 0.5 mm<br>Volume dried: 500 ml |
| 11 | Ceftazidime | Ceftazidime 2.405<br>Lactose 2.115<br>Tween 80 0.48 | Spray drying | Solvent: water<br>Conc. Solids: 1% weight/vol<br>Spray temperature: 130° C.<br>Feed flow: 3 ml/min<br>Nozzle diameter: 1 mm<br>Volume dried: 500 ml |
| 12 | BDP | BDP 0.05<br>Span 20 0.02<br>Tween 20 0.1<br>NaCl 1.125<br>Lactose 8.705 | Spray drying | Solvent: water/ethanol 30/70<br>Conc. Solids: 1% weight/vol<br>Spray temperature: 130° C.<br>Feed flow: 4 ml/min<br>Nozzle diameter: 0.5 mm<br>Volume dried: 1000 ml |
| 13 | Budesonide | Budesonide 0.25<br>Tween 80 0.5<br>Lactose 24.25 | Spray drying | Solvent: water/ethanol 70/30<br>Conc. Solids: 5%<br>Spray temperature: 130° C.<br>Feed flow: 3 ml/min<br>Nozzle diameter: 0.5 mm<br>Volume dried: 500 ml |
| 14 | Budesonide | Budesonide 0.25<br>Tween 80 0.5<br>Maltodextrin 24.25 | Spray drying | Solvent: water/ethanol 70/30<br>Conc. Solids: 5%<br>Spray temperature: 130° C.<br>Feed flow: 3 ml/min<br>Nozzle diameter: 0.5 mm<br>Volume dried: 500 ml |
| 15 | Budesonide | Budesonide 0.3<br>Tween 80 0.075<br>L-Leucine 1.5<br>Lactose 13.125 | Spray drying | Solvent: water/ethanol 70/30<br>Conc. Solids: 5%<br>Spray temperature: 130° C.<br>Feed flow: 3 ml/min<br>Nozzle diameter: 0.5 mm<br>Volume dried: 300 ml |
| 16 | Budesonide | Budesonide 0.15<br>Tween 80 0.075<br>L-Leucine 1.5<br>Lactose 13.275 | Spray drying | Solvent: water/ethanol 70/30<br>Conc. Solids: 5%<br>Spray temperature: 130° C.<br>Feed flow: 3 ml/min<br>Nozzle diameter: 0.5 mm<br>Volume dried: 300 ml |
| 17 | Formoterol | Formoterol fum. 0.012<br>Tween 80 0.075<br>L-Leucine 2.25<br>Lactose 12.663 | Spray drying | Solvent: water/ethanol 80/20<br>Conc. Solids: 3%<br>Spray temperature: 130° C.<br>Feed flow: 2 ml/min<br>Nozzle diameter: 0.5 mm<br>Volume dried: 500 ml |
| 18 | Formoterol | Formoterol fum. 0.012<br>Tween 80 0.075<br>L-Leucine 4.5<br>Lactose 10.413 | Spray drying | Solvent: water/ethanol 80/20<br>Conc. Solids: 3%<br>Spray temperature: 130° C.<br>Feed flow: 2 ml/min<br>Nozzle diameter: 0.5 mm<br>Volume dried: 500 ml |
| 19 | Insulin | Insulin 1.5<br>Tween 80 0.075<br>L-Leucine 1.5<br>Lactose 11.93 | Spray drying | Solvent: water + HCl + NaOH until insulin dissolution.<br>Conc. Solids: 3%<br>Spray temperature: 130° C.<br>Feed flow: 3 ml/min<br>Nozzle diameter: 1 mm<br>Volume dried: 500 ml |

TABLE 2-continued preparation

| Example | Active ingredient | Composition (g) | Preparation method | Operative conditions |
|---|---|---|---|---|
| 20 | Insulin | Insulin 0.525<br>Tween 80 0.075<br>L-Leucine 1.5<br>Lactose 12.9 | Spray drying | Solvent: water + HCl + NaOH until insulin dissolution.<br>Conc. Solids: 3%<br>Spray temperature: 130° C.<br>Feed flow: 3 ml/min<br>Nozzle diameter: 1 mm<br>Volume dried: 500 ml |
| 21 | Ceftazidime | Ceftazidime 7.5<br>Tween 80 0.075<br>L-Leucine 2.25<br>Lactose 5.175 | Spray drying | Solvent: water<br>Conc. Solids: 3%<br>Spray temperature: 130° C.<br>Feed flow: 3 ml/min<br>Nozzle diameter: 0.5 mm<br>Volume dried: 500 ml |
| 22 | Colistine | Colistine 6<br>Tween 80 0.06<br>L-Leucine 2.25<br>Lactose 6.69 | Spray drying | Solvent: water<br>Conc. Solids: 3%<br>Spray temperature: 130° C.<br>Feed flow: 3 ml/min<br>Nozzle diameter: 0.5 mm<br>Volume dried: 500 ml |
| 23 | Ceftazidime | Ceftazidime 6<br>Tween 80 0.060<br>L-Leucine 4.5<br>Lactose 4.44 | Spray drying | Solvent: water<br>Conc. Solids: 3%<br>Spray temperature: 130° C.<br>Feed flow: 3 ml/min<br>Nozzle diameter: 0.5 mm<br>Volume dried: 500 ml |
| 24 | Ceftazidime | Ceftazidime 3<br>Tween 80 0.075<br>L-Leucine 2.25<br>Lactose 9.675 | Spray drying | Solvent: water<br>Conc. Solids: 3%<br>Spray temperature: 130° C.<br>Feed flow: 3 ml/min<br>Nozzle diameter: 0.5 mm<br>Volume dried: 500 ml |
| 25 | Ceftazidime | Ceftazidime 7.128<br>L-Leucine 1.8<br>Tween 80 0.072 | Spray drying | Solvent: water<br>Conc. Solids: 3%<br>Spray temperature: 130° C.<br>Feed flow: 3 ml/min<br>Nozzle diameter: 0.5 mm<br>Volume dried: 300 ml |
| 26 | Ceftazidime | Ceftazidime 7.569<br>L-Leucine 1.35<br>Tween 80 0.081 | Spray drying | Solvent: water<br>Conc. Solids: 3%<br>Spray temperature: 130° C.<br>Feed flow: 3 ml/min<br>Nozzle diameter: 0.5 mm<br>Volume dried: 300 ml |

Demonstration of the General Improvement of the Pulmonary Deposition

To perform the test a Multi Stage Liquid Impinger apparatus working at 30 liters per minute was used.

An amount of 100 mg of powder was dissolved/dispersed in 2 ml of distilled water, as in examples 1, 2, 5, 7, 8, 11, 13 and 14. an amount of 160 mg was instead dissolved or dispersed in 2 ml, as in examples 6, 9 and 12, while, as in example 10, 125 mg of powder were dissolved in 2 ml of distilled water.

The obtained solution/suspension was transferred to a nebulizer ampoule C and the nebulizer was connected to the Multi Stage Liquid Impinger. After starting the vacuum pump, connected to the Multi Stage, the nebulizer was activated for a total time of 5 minutes. At last, the nebulizer was switched off, followed by the vacuum pump. After 30 minutes the Multi Stage was disassembled and the amount of the active ingredient dissolved in each stage was measured by mean of a suitable chromatographic conditions.

It is important to notice that from in vitro tests performed either with MSLI or Andersen cascade impactor the MMAD (Mass Median Aerodynamic Diameter) value doesn't provide any information on the deposition pattern of the nebulized product delivered from the nebulizer.

The MMAD is a median parameter that only indicates the position of the 50% of the size distribution of the droplets emitted in the impinger, but does not represent a real measurement of the particle size of the delivered particles, since in the case of a nebulizer one can always increase the delivery time and consequently increase the amount delivered to the deep stages (4 and 5), consequently resulting in a reduced MMAD value.

For this reason the characterization of the delivered formulations must be carried out directly measuring the nebulized droplet's size.

It is moreover important to notice that the in vitro test, through the MMAD, produces a measure of the features of the nebulized product without considering the amount of drug delivered and therefore of the actually active dose that reaches the lung target (in this case <5.0 μm).

It was therefore possible to define the active dose of drug (A.F. or Active Fraction) through the formula:

$$A.F.=(D.F.\times F.P.F)/100.$$

Where:

A.F.=Active Fraction or % fraction actually active on the target site

D.F.=Delivered Fraction or % fraction of drug delivered from the nebulizer

F.P.F.=Fine Particle Fraction or % fraction of the delivered amount which is active in the target site This calculation allows to find significant differences between the amount of drug actually delivered to the target site and the amount in the nebulizer, that in all these case was the same one.

It can be seen that the delivered amount when lactose and surfactant are included in the formulation is often double than the one in formulation without lactose/surfactant and with salts.

Such effect is necessarily due to a combined effect of the increase of the delivered amount and of the reduction of the particle size of the delivered product. The results are shown in Table 3 below.

Multi Stage Liquid Impinger. The capsule was pierced and a vacuum was applied through the Multi Stage Liquid Impinger in order to provide an air flow through the device of 60 Liters per minute for 4 seconds. These operations were repeated with 5 to 10 capsules in order to aerosolize a sufficient amount of powder in the system for analytical detection. After the last capsule had been aerosolized through the system the Multi Stage Liquid Impinger was kept at rest for at least 30 minutes. Subsequently the Multi Stage was disassembled and the amount of active ingredient dissolved in each stage was measured by mean of a suitable chromatographic conditions.

In similar was as described for nebulized formulations, it was possible to define the active dose of drug (A.F. or Active Fraction) through the formula:

$$A.F.=(D.F.\times F.P.F)/100.$$

TABLE 3

| Ex. | Active ingredient | Nebulizer | Time of nebulization (min) | Delivered Fraction (%) | Fine Particle Fraction (%) | MMAD (μm) | Active Fraction AF = (DF × FPF)/100 (%) |
|---|---|---|---|---|---|---|---|
| Ref. A | BDP | Clenny | 5 | 49.0 | 29.1 | 6.99 | 14.3 |
| 6 | BDP | Clenny | 5 | 65.2 | 48.3 | 4.75 | 31.5 |
| Ref. B | BDP | Clenny | 5 | 53.6 | 35.4 | 6.16 | 19.0 |
| Ref. C | Budesonide | Clenny | 5 | 39.2 | 27.3 | 7.25 | 10.7 |
| 7 | Budesonide | Clenny | 5 | 65.7 | 52.4 | 4.14 | 34.4 |
| Ref. D | Budesonide | Clenny | 5 | 67.2 | 29.3 | 7.16 | 19.7 |
| 5 | Formoterol | Clenny | 5 | 61.9 | 60.5 | 3.15 | 37.4 |
| Ref. E | Formoterol | Clenny | 5 | 54.6 | 43.3 | 4.96 | 23.6 |
| Ref. F | Formoterol | Clenny | 5 | 69.1 | 59.5 | 3.25 | 41.1 |
| 2 | Formoterol | Clenny | 5 | 63.1 | 74.3 | 1.94 | 46.9 |
| 2 | Budesonide | Clenny | 5 | 56.2 | 69.4 | 2.56 | 39.0 |
| 1 | Formoterol | Clenny | 5 | 69.8 | 58.0 | 3.69 | 40.4 |
| 1 | Budesonide | Clenny | 5 | 62.8 | 49.8 | 4.53 | 31.3 |
| 8 | Budesonide | Clenny | 5 | 64.7 | 51.2 | 4.28 | 33.1 |
| 8 | Salbutamol | Clenny | 5 | 68.1 | 54.3 | 3.92 | 37.0 |
| Ref. G | Salbutamol | Clenny | 5 | 46.3 | 54.7 | 3.61 | 25.3 |
| 9 | Salbutamol | Clenny | 5 | 67.4 | 59.0 | 3.42 | 39.8 |
| 9 | BDP | Clenny | 5 | 61.7 | 50.4 | 4.37 | 31.1 |
| 10 | Salbutamol | Clenny | 5 | 69.3 | 49.1 | 4.58 | 34.0 |
| 11 | Ceftazidime | Clenny | 5 | 75.3 | 46.8 | 4.91 | 35.2 |
| Ref H | BDP | Microair | 10 | 20.9 | 62.5 | 1.26 | 13.1 |
| 12 | BDP | Microair | 10 | 43.7 | 57.8 | 2.56 | 25.3 |
| Ref I | Budesonide | Microair | 10 | 36.7 | 43.1 | 3.01 | 15.9 |
| 13 | Budesonide | Microair | 10 | 35.7 | 70.5 | 2.44 | 25.1 |
| Ref. J | Salbutamol | Clenny | 5 | 65.3 | 59.0 | 3.36 | 38.5 |
| 14 | Budesonide | Aeroneb Go | 5 | 83.5 | 42.1 | 5.53 | 35.1 |

To perform the test a Multi Stage Liquid Impinger apparatus as described by the European Pharmacopoeia working at 60 liters per minute was used.

A variable amount of powder ranging between 15 and 25 mg was loaded in size #3 gelatine capsules as in examples 15 to 26.

A single capsule was transferred to an Aerolizer® dry powder inhalation device and the device was connected to the Where:

A.F.=Active Fraction or % fraction actually active on the target site

D.F.=Delivered Fraction or % fraction of drug delivered from the dry powder inhaler F.P.F.=Fine Particle Fraction or % fraction of the delivered amount which is active in the target site. The results are shown in Table 4 below.

TABLE 4

| Example | Active ingredient | Device/ Flow rate (Lpm) | Flow rate (Litres/min) | Delivered Fraction (%) | Fine Particle Fraction (%) | MMAD (μm) | Active Fraction AF = (DF × FPF) * 100 (%) |
|---|---|---|---|---|---|---|---|
| Ref. K | Budesonide | Aerolizer | 60 | 83.0 | 12.6 | 5.89 | 10.5 |
| 15 | Budesonide | Aerolizer | 60 | 90.5 | 42.8 | 4.49 | 38.7 |
| 16 | Budesonide | Aerolizer | 60 | 90.1 | 54.1 | 3.83 | 48.7 |
| Ref. L | Formoterol | Aerolizer | 60 | 89.1 | 19.3 | 6.05 | 17.2 |

TABLE 4-continued

| Example | Active ingredient | Device/ Flow rate (Lpm) | Flow rate (Litres/min) | Delivered Fraction (%) | Fine Particle Fraction (%) | MMAD (μm) | Active Fraction AF = (DF × FPF) * 100 (%) |
|---|---|---|---|---|---|---|---|
| 17 | Formoterol | Aerolizer | 60 | 85.3 | 50.8 | 4.17 | 43.3 |
| 18 | Formoterol | Aerolizer | 60 | 88.5 | 51.8 | 4.08 | 45.8 |
| 19 | Insulin | Aerolizer | 60 | 83.0 | 43.4 | 4.46 | 36.0 |
| 20 | Insulin | Aerolizer | 60 | 85.8 | 52.3 | 4.10 | 44.9 |
| 21 | Ceftazidime | Aerolizer | 60 | 89.2 | 44.7 | 4.61 | 39.9 |
| 22 | Colistine | Aerolizer | 60 | 85.0 | 39.2 | 4.07 | 33.3 |
| 23 | Ceftazidime | Aerolizer | 60 | 93.0 | 47.0 | 4.26 | 43.7 |
| 24 | Ceftazidime | Aerolizer | 60 | 89.3 | 47.4 | 4.49 | 42.3 |
| 25 | Ceftazidime | Aerolizer | 60 | 93.1 | 52.9 | 3.77 | 49.2 |
| 26 | Ceftazidime | Aerolizer | 60 | 91.8 | 45.3 | 4.41 | 41.6 |

Composition of the reference examples, not according to the invention:

Ref.A: commercial product Clenil A (Chiesi), suspension to be nebulized of BDP 0.8 mg/ml containing Tween 20, 1 mg/ml; Span 20, 0.2 mg/ml; NaCl 4.2 mg/ml and Purified Water, tested with nebulizer Clenny® Medel Ref.B: inhalatory suspension of BDP 0.8 mg/ml containing Tween 20, 1 mg/ml; Span 20, 0.2 mg/ml; NaCl 4.2 mg/ml; $Na_2HPO_4$ 7.24 mg/ml; $KH_2PO_4$ 3.54 mg/ml and Purified Water, tested with nebulizer Clenny® Medel.

Ref.C: commercial product Pulmaxan (Astra Zeneca), suspension to be nebulized of budesonide 1.0 mg/2 ml. containing Tween 80 0.2 mg/ml; EDTA 0.1 mg/ml; NaCl 8.5 mg/ml; anidrous citric acid 0.28 mg/ml; sodium citrate 0.5 mg/ml and Purified Water, tested with nebulizer Clenny® Medel.

Ref.D: non commercial inhalatory suspension of budesonide 1.0 mg/2 ml containing: Tween 80 0.2 mg/ml; EDTA 0.1 mg/ml; NaCl 8.5 mg/ml; anidrous citric acid 0.28 mg/ml; sodium citrate 0.5 mg/ml; Metil paraben 1.35 mg/ml; Propil paraben 0.15 mg/ml and Purified Water, tested with nebulizer Clenny® Medel.

Ref.E: aqueous solution of formoterol fumarate 24 μg/2 ml containing Tween 80 1 mg/ml tested with nebulizer Clenny® Medel.

Ref.F: aqueous solution of formoterol fumarate, lactose and tween 80 having the same composition as example 5 and tested with nebulizer Clenny® Medel.

Ref.G: commercial product Broncovaleas (Valeas), aqueous solution to be nebulized, with salbutamol sulphate in water as such as to have a final concentration of 200 μg/2 ml tested with nebulizer Clenny® Medel Ref.H: commercial product Clenil A (Chiesi), suspension to be nebulized of BDP 0.8 mg/ml containing Tween 20, 1 mg/ml; Span 20, 0.2 mg/ml; NaCl 4.2 mg/ml and purified water, tested with nebulizer MicroAir® Omron Ref.I: commercial product Pulmaxan (Astra Zeneca), suspension to be nebulized of budesonide 1.0 mg/2 ml containing Tween 80 0.2 mg/ml; EDTA 0.1 mg/ml; NaCl 8.5 mg/ml; anidrous citric acid 0.28 mg/ml; sodium citrate 0.5 mg/ml and purified water, tested with nebulizer MicroAir® Omron.

Ref.J: non commercial inhalatory suspension of salbutamol 2.5 mg/2 ml containing Tween 80 1 mg/ml and Lactose 4.77 mg/ml.

Ref.K: commercial product Miflonide® (Novartis), inhalatory powder of budesonide 400 mcg/cps.

Ref.L: commercial product Foradil® (Novartis), inhalatory powder of formoterol fumarate 12 mcg/cps.

The invention claimed is:

1. Inhalatory pharmaceutical composition in solid dry powder form comprising a drug, a soluble solid excipient and a surfactant, said composition being prepared through spray drying, characterized by:
   said soluble solid excipient comprises leucine which is present in an amount between 10% and less than 100% by weight; said solid excipient forming a solid matrix in which said drug is dispersed;
   the weight ratio between said surfactant and said drug is between 0.01 and 10;
   the particle size of at least 50% of the particles of said powder is below 5 μm;
   the bulk density $d_b$ of said powder is between 0.1 and 0.3 g/cc;
   the tapped density $d_t$ of said powder is between 0.15 and 0.7 g/cc
   the ratio $d_b/d_t$ is between 0.2 and 0.65; and
   wherein said excipient and said surfactant do not include phospholipids.

2. Inhalatory composition according to claim 1, characterized in that said soluble solid excipient is present in an amount between 40% and 99.9%.

3. Inhalatory composition according to claim 1, characterized in that said drug is hydrophilic.

4. Inhalatory composition according to claim 1, characterized in that said drug is an association of a hydrophilic drug and a hydrophobic drug.

5. Inhalatory composition according to claim 1, characterized in that said excipient is a sugar.

6. Inhalatory composition according to claim 5, characterized in that said sugar is lactose.

7. Inhalatory composition according to claim 1, characterized in that said excipient is an aminoacid.

8. Inhalatory composition according to claim 7, characterized in that said aminoacid is selected from the group consisting of N-acetylcysteine and carbocysteine.

9. Inhalatory composition according to claim 1, characterized in that said weight ratio between said surfactant and said drug is between 0.2 and 7.

10. Inhalatory composition according to claim 9, characterized in that said weight ratio between said surfactant and said drug is between 0.5 and 3.

11. Inhalatory composition according to claim 1, characterized by comprising particles with a shape about spherical and internally hollow.

12. Inhalatory composition according to claim 1, characterized in that said drug is selected from the classes of the $\beta_2$ agonists and steroids.

13. Inhalatory composition according to claim 12, characterized in that said drug is selected from the group consisting of salbutamol, salmeterol, formoterol, fenoterol, beclomethasone, budesonide, fluticasone and pharmaceutically acceptable derivatives thereof.

14. Composition of a drug in a liquid medium obtainable by extemporaneously dispersing a dry powder comprising a drug, a soluble solid excipient and a surfactant, said dry powder being prepared through spray drying, characterized in that:
said soluble solid excipient comprises leucine which is present in an amount between 10% and less than 100% by weight; said solid excipient forming a solid matrix in which said drug is dispersed;
the weight ratio between said surfactant and said drug is between 0.01 and 10;

the particle size of at least 50% of the particles of said powder is below 5 μm;

the bulk density $d_b$ of said powder is between 0.1 and 0.3 g/cc;

the tapped density $d_t$ of said powder is between 0.15 and 0.7 g/cc the ratio $d_b/d_t$ is between 0.2 and 0.65; and wherein said excipient and said surfactant do not include phospholipids.

15. Composition according to claim 14, characterized in that said drug is suspended in said liquid medium.

16. Composition according to claim 14, characterized in that said drug is dissolved in said liquid medium.

17. Composition according to claim 14 for inhalatory administration.

18. Inhalatory composition according to claim 17, characterized in that a delivery by pneumatic nebulizer of a standard dose of said solution or suspension in a Multi Stage liquid Impinger working at 30 l/m for 5 minutes generates a deposited fraction in said Multi Stage liquid Impinger calculated as Active Fraction (A.F.) of at least 25%.

19. Composition according to claim 18 for parenteral or enteral administration.

20. Process for preparing an inhalatory composition of a drug in the form of dry powder, comprising a drug, a soluble solid excipient and a surfactant, wherein:

said soluble solid excipient comprises leucine which is present in an amount between 10% and less than 100% by weight; said solid excipient forming a solid matrix in which said drug is dispersed;

the weight ratio between said surfactant and said drug is between 0.01 and 10;

the particle size of at least 50% of the particles of said powder is below 5 μm;

the bulk density $d_b$ of said powder is between 0.1 and 0.3 g/cc;

the tapped density $d_t$ of said powder is between 0.15 and 0.7 g/cc;

the ratio $d_b/d_t$ is between 0.2 and 0.65; and wherein said excipient and said surfactant do not include phospholipids, characterized by comprising the steps of:

a) preparing a first phase (A) in which an active ingredient is in an appropriate liquid medium;

b) preparing a second phase (B) in which soluble solid excipients are dissolved and surfactants are dissolved or dispersed in an aqueous medium;

c) mixing said phases (A) and (B) to obtain a third phase (C) consisting of a homogeneous liquid medium;

d) drying said phase (C) in controlled conditions which comprise comprises a removal of liquid medium, solvent or dispersing agent from phase (C) by spray-drying to obtain a dry powder with a mean particles size lower than 15 μm; characterized in that said step d) collecting said dry powder and stocking it in an appropriate way for an extemporaneous preparation of a suspension.

21. Process for preparing an inhalatory composition of a drug according to claim 20, characterized in that said phase (A) can be either a suspension or a solution of an active ingredient in an appropriate liquid medium.

22. Process according to claim 20, characterized in that said phase (A) is a solution.

23. Process according to claim 22, characterized in that said solution is a solution in an organic solvent selected among those miscible with water.

24. Process according to claim 20, characterized in that the total amount of drug, excipient and surfactant in said phase (C) is from 1 to 5% weight/volume.

25. Process according to claim 24, characterized in that the total amount of drug, excipient and surfactant in said phase (C) is from 3 to 5% weight/volume.

26. Kit for the administration of a drug in a powder form or in aqueous dispersion comprising a dosed amount of the composition according to claim 1, and a dosed amount of a liquid medium as solvent or dispersing medium.

27. Kit according to claim 26, comprising a delivery device characterized by comprising a tube (10) having a middle portion with enlarged diameter, a lower seal (17) slidable upon external operation and a middle seal (15) also slidable in said tube, said tube being closed by a seal (26) that can be pierced with a mouthpiece (28, 28') provided with a piercing rod (30), whereby the powder or the dispersion or solution of the powder in a liquid medium is delivered and administered to a patient.

28. Kit according to claim 26, wherein said mouthpiece for delivering said inhalatory powder is provided with a set of holes (32) for air inlet.

29. Inhalatory pharmaceutical composition according to claim 1, characterized in that said drug is diluted within said excipient according to a dilution factor defined as the ratio between the mass of powder and the mass of active drug comprised within 1.18 and 500000, wherein the fine particle dose less than 5.0 μm expressed as number of particles is comprised between $3.8\times10^6$ and $5.1\times10^{13}$.

30. Inhalatory composition according to claim 29, characterized by a dose of active drug in the range 0.1-1 μg diluted within an excipient according to a dilution factor within 5000 and 500000, wherein fine particle dose less than 5.0 μm expressed as number of particles is comprised between $3.8\times10^6$ and $5.1\times10^{11}$.

31. Inhalatory composition according to claim 29, characterized by a dose of active drug in the range 1-10 μg diluted within an excipient according to a dilution factor within 50 and 50000, wherein fine particle dose less than 5.0 μm expressed as number of particles is comprised between $3.8\times10^6$ and $5.1\times10^{11}$.

32. Inhalatory composition according to claim 29, characterized by a dose of active drug in the range 10-100 μg diluted within an excipient according to a dilution factor within 5 and 5000, wherein fine particle dose less than 5.0 μm expressed as number of particles is comprised between $3.8\times10^6$ and $5.1\times10^{11}$.

33. Inhalatory composition according to claim 29, characterized by a dose of active drug in the range 100 μg-1 mg diluted within an excipient according to a dilution factor within 1.18 and 500, wherein fine particle dose less than 5.0 μm expressed as number of particles is comprised between $9.0\times10^6$ and $5.1\times10^{11}$.

34. Inhalatory composition according to claim 29, characterized by a dose of active drug in the range 1-10 mg diluted within an excipient according to a dilution factor within 1.18 and 50, wherein fine particle dose less than 5.0 μm expressed as number of particles is comprised between $9.0 \times 10^6$ and $5.1 \times 10^{11}$.

35. Inhalatory composition according to claim 29, characterized by a dose of active drug in the range 10-100 mg diluted within an excipient according to a dilution factor within 1.18 and 50, wherein fine particle dose less than 5.0 μm expressed as number of particles is comprised between $3.8 \times 10^6$ and $5.1 \times 10^{11}$ $9.0 \times 10^8$ and $5.1 \times 10^{12}$.

36. Inhalatory composition according to claim 29, characterized by a dose of active drug in the range 100 mg-1 g diluted within an excipient according to a dilution factor within 1.18 and 50, wherein fine particle dose less than 5.0 μm expressed as number of particles is comprised between $9.0 \times 10^9$ and $5.1 \times 10^{13}$.

37. Inhalatory composition according to claim 5, characterized by being in a liquid medium for use in a nebulizer.

38. Inhalatory composition according to claim 37, wherein said sugar is lactose.

39. Inhalatory composition according to claim 37 wherein said sugar is maltodextrin.

40. Inhalatory composition according to claim 1, wherein said drug is selected from the group consisting of ceftazidime, colistine, tobramicine and tobramycin sulphate.

* * * * *